(12) United States Patent
Kronowitz

(10) Patent No.: US 9,468,519 B2
(45) Date of Patent: *Oct. 18, 2016

(54) METHODS AND SYSTEMS FOR BREAST RECONSTRUCTION

(71) Applicant: Steven J. Kronowitz, Houston, TX (US)

(72) Inventor: Steven J. Kronowitz, Houston, TX (US)

(73) Assignee: Steven Kronowitz, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/171,259

(22) Filed: Feb. 3, 2014

(65) Prior Publication Data

US 2014/0222145 A1  Aug. 7, 2014

Related U.S. Application Data

(63) Continuation of application No. 13/220,426, filed on Aug. 29, 2011, now Pat. No. 8,641,759, which is a continuation of application No. 12/063,403, filed as application No. PCT/US2006/031091 on Aug. 9, 2006, now Pat. No. 8,080,057.

(60) Provisional application No. 60/737,657, filed on Nov. 17, 2005, provisional application No. 60/706,543, filed on Aug. 9, 2005.

(51) Int. Cl.
  *A61F 2/12* (2006.01)
  *A61M 39/02* (2006.01)
  *A61N 5/10* (2006.01)

(52) U.S. Cl.
  CPC .............. *A61F 2/12* (2013.01); *A61M 39/02* (2013.01); *A61M 39/0208* (2013.01); *A61N 5/1007* (2013.01); *A61N 5/1015* (2013.01)

(58) Field of Classification Search
  CPC .................................... A61F 2/12; A61F 2/52
  USPC ............................................. 623/7–8
  See application file for complete search history.

(56) References Cited

U.S. PATENT DOCUMENTS

| | | | | |
|---|---|---|---|---|
| 5,201,715 A | * | 4/1993 | Masters | 604/175 |
| 5,207,709 A | * | 5/1993 | Picha | 623/23.74 |
| 5,759,204 A | * | 6/1998 | Seare, Jr. | 623/11.11 |
| 6,066,856 A | * | 5/2000 | Fishman | 250/519.1 |
| 6,071,309 A | * | 6/2000 | Knowlton | 623/8 |
| 6,206,930 B1 | * | 3/2001 | Burg et al. | 623/23.64 |
| 6,315,796 B1 | * | 11/2001 | Eaton | 623/8 |
| 8,080,057 B2 | * | 12/2011 | Kronowitz | 623/8 |
| 8,394,118 B2 | * | 3/2013 | Jones et al. | 606/192 |
| 8,641,759 B2 | * | 2/2014 | Kronowitz | 623/8 |

(Continued)

*Primary Examiner* — Suzette J Gherbi

(74) *Attorney, Agent, or Firm* — Conley Rose, P.C.

(57) ABSTRACT

Methods for optimal breast reconstruction are disclosed. The methods include steps for performing a mastectomy that preserves a breast skin envelope. A prosthesis may be inserted into the breast and may be inflated to preserve the shape of the breast skin envelope. The prosthesis may include, a base, a balloon coupled to the base, where the balloon may be inflated to preserve the shape of the breast skin envelope. The prosthesis may also include tube coupled to port for filling the balloon to a predetermined volume. A needle-lock system, coupled to the port may be used to inject, for example, fluids into the balloon. If a patient requires post-mastectomy radiation, breast reconstruction may be delayed and the prosthesis may remain in the breast cavity during the treatment. The treatment may be external beam radiation. Alternatively, the treatment may include brachytherapy technique for treating the internal breast cavity.

19 Claims, 24 Drawing Sheets

(56) References Cited

U.S. PATENT DOCUMENTS

| | | | |
|---|---|---|---|
| 2001/0037046 A1* | 11/2001 | Weinberger et al. | 600/3 |
| 2002/0010383 A1* | 1/2002 | Weinberger | 600/3 |
| 2004/0049269 A1* | 3/2004 | Corbitt et al. | 623/8 |
| 2005/0240074 A1* | 10/2005 | Lubock | 600/3 |
| 2006/0190022 A1* | 8/2006 | Beyar et al. | 606/192 |
| 2006/0271024 A1* | 11/2006 | Gertner et al. | 606/2 |
| 2007/0167668 A1* | 7/2007 | White et al. | 600/3 |
| 2007/0270627 A1* | 11/2007 | Cutrer et al. | 600/7 |
| 2007/0270635 A1* | 11/2007 | Schellenberg | 600/101 |
| 2012/0123535 A1* | 5/2012 | Alejandro | 623/8 |
| 2014/0221732 A1* | 8/2014 | Dayton et al. | 600/30 |

* cited by examiner

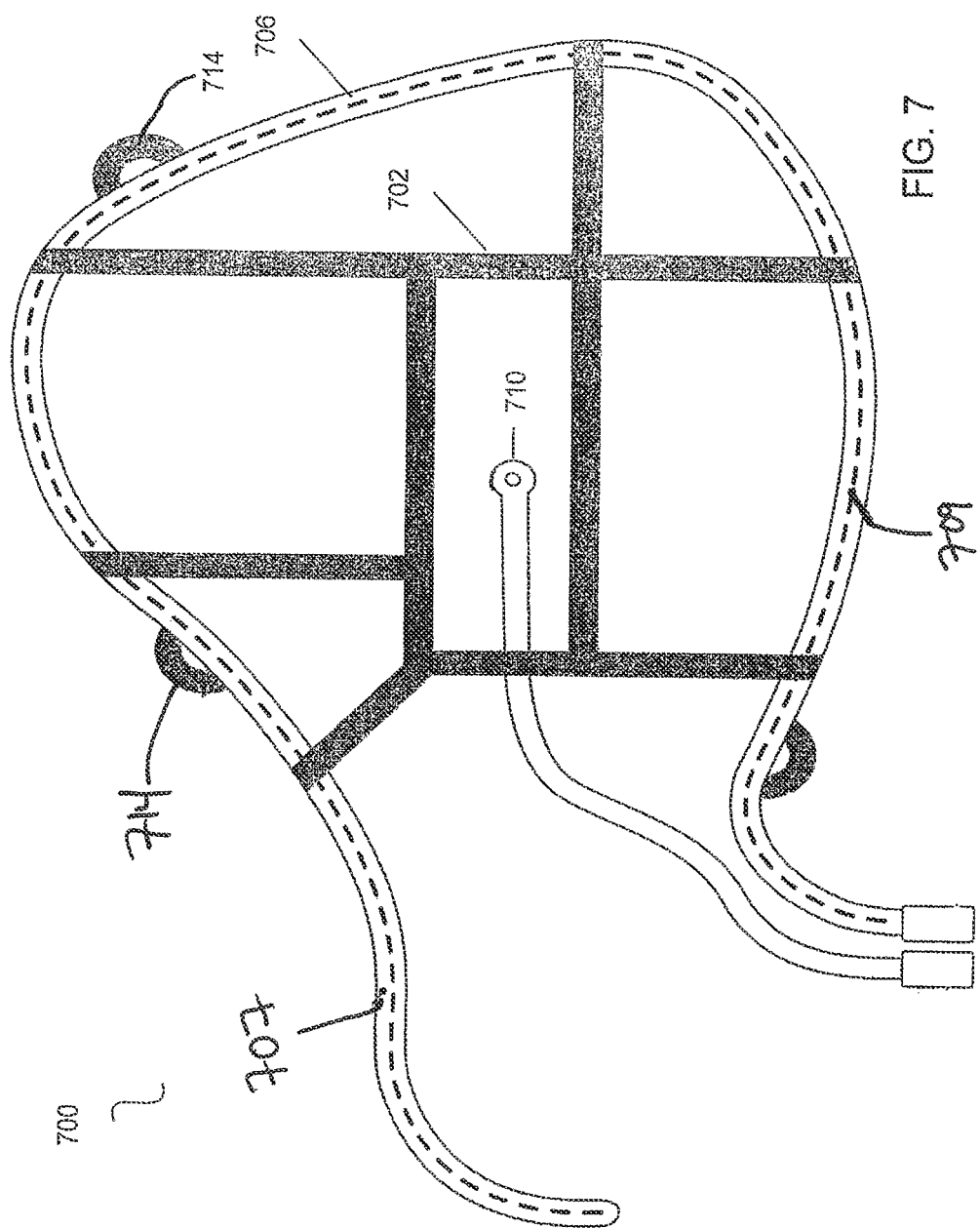

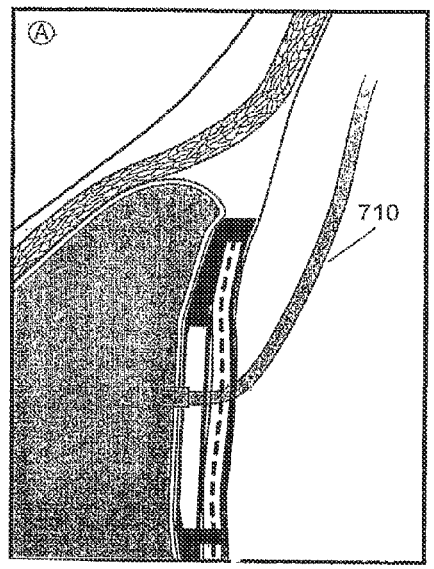
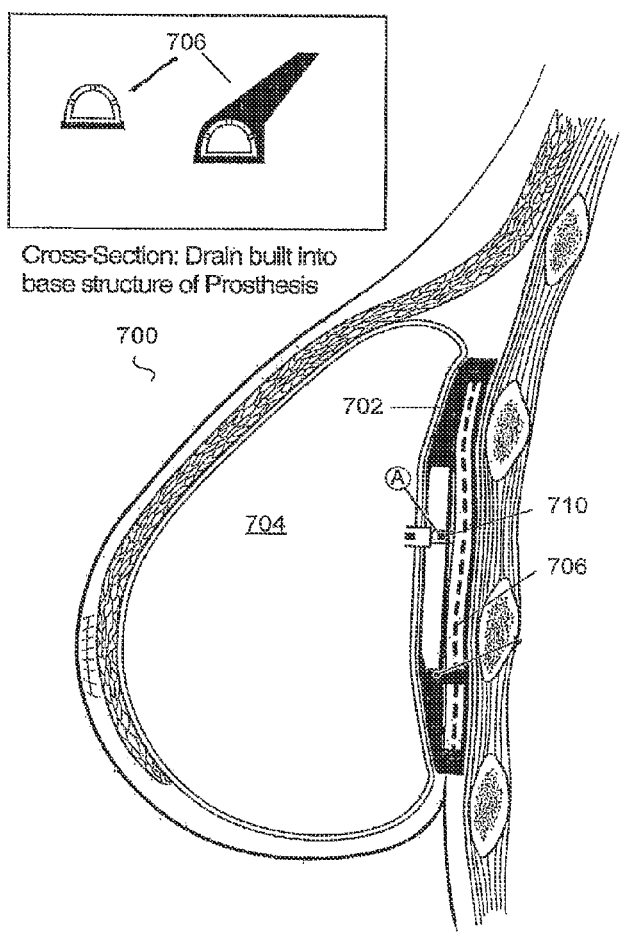
FIG. 8C
FIG. 8B
Cross-Section: Drain built into base structure of Prosthesis
FIG. 8A

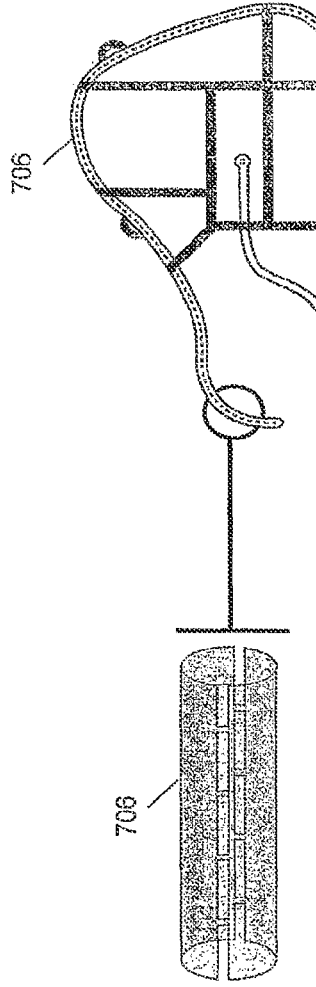
FIG. 9
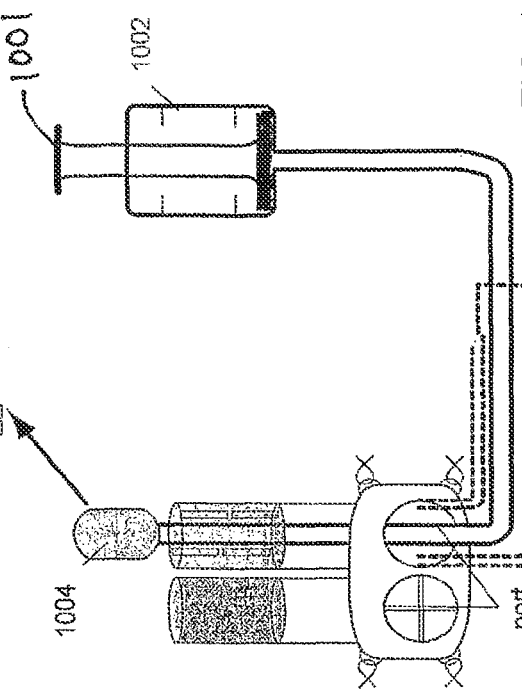
FIG. 13A
FIG. 13B

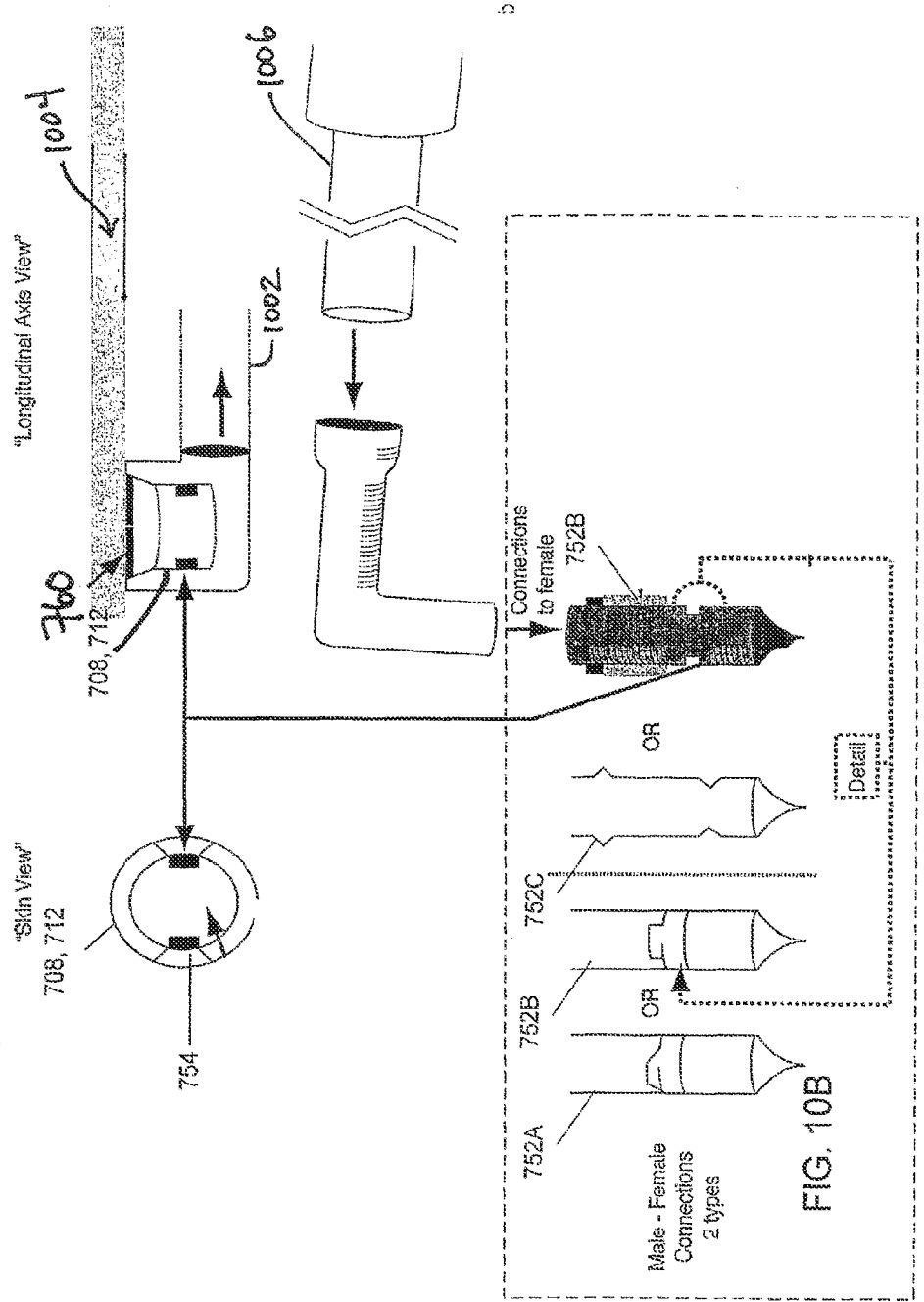

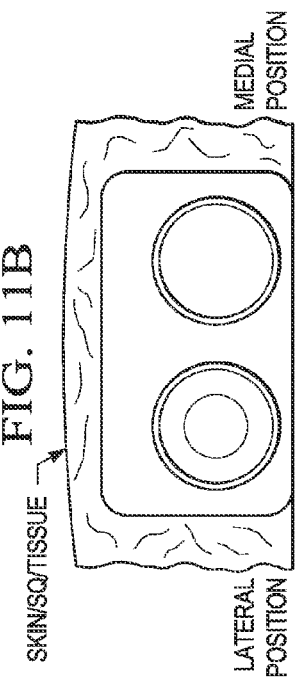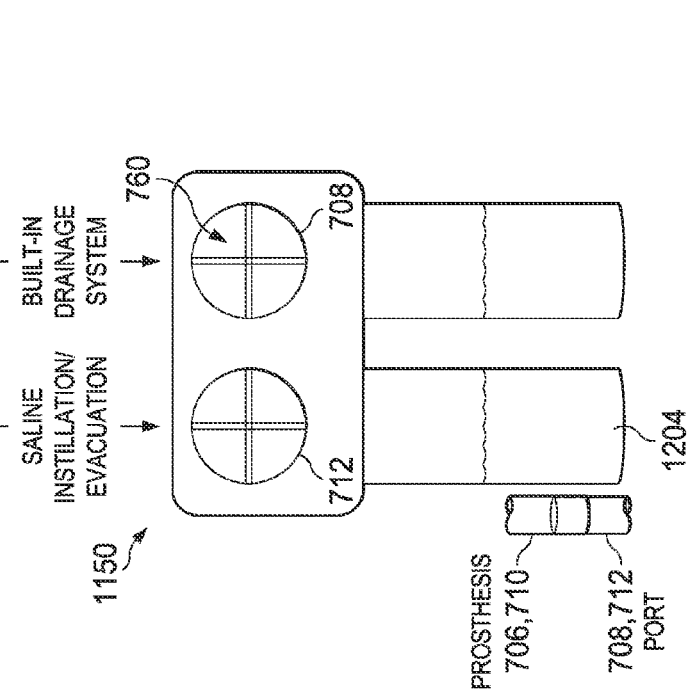
FIG. 11A
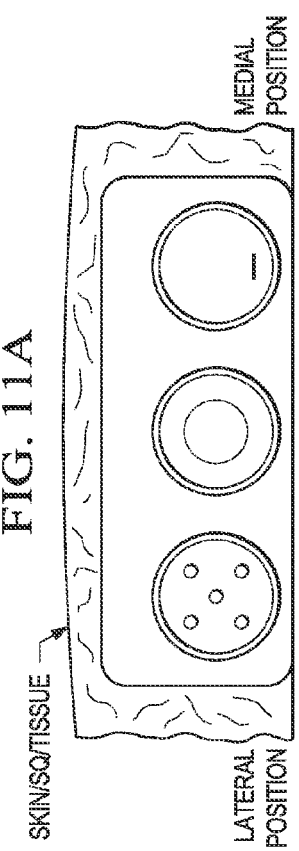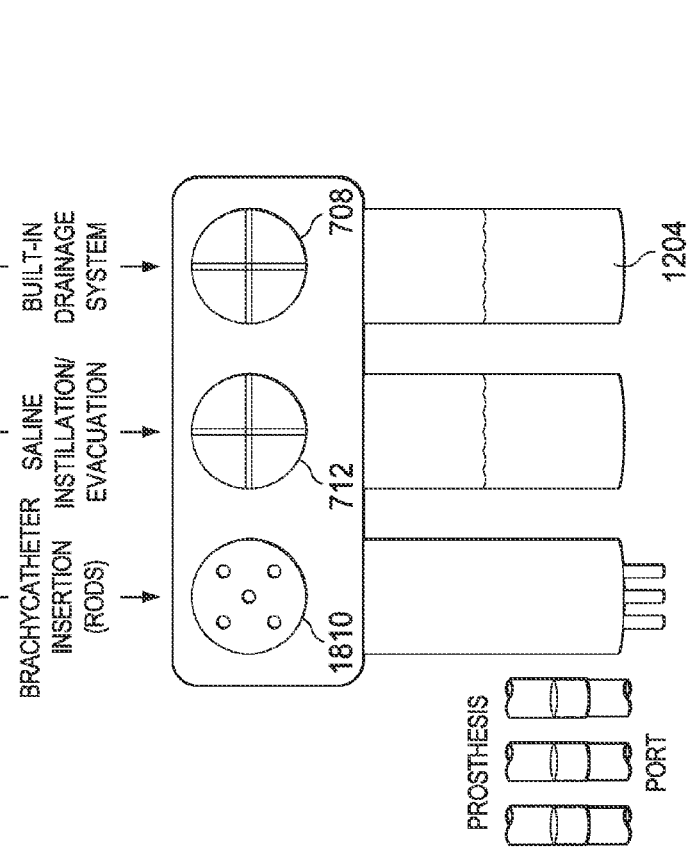
FIG. 11B

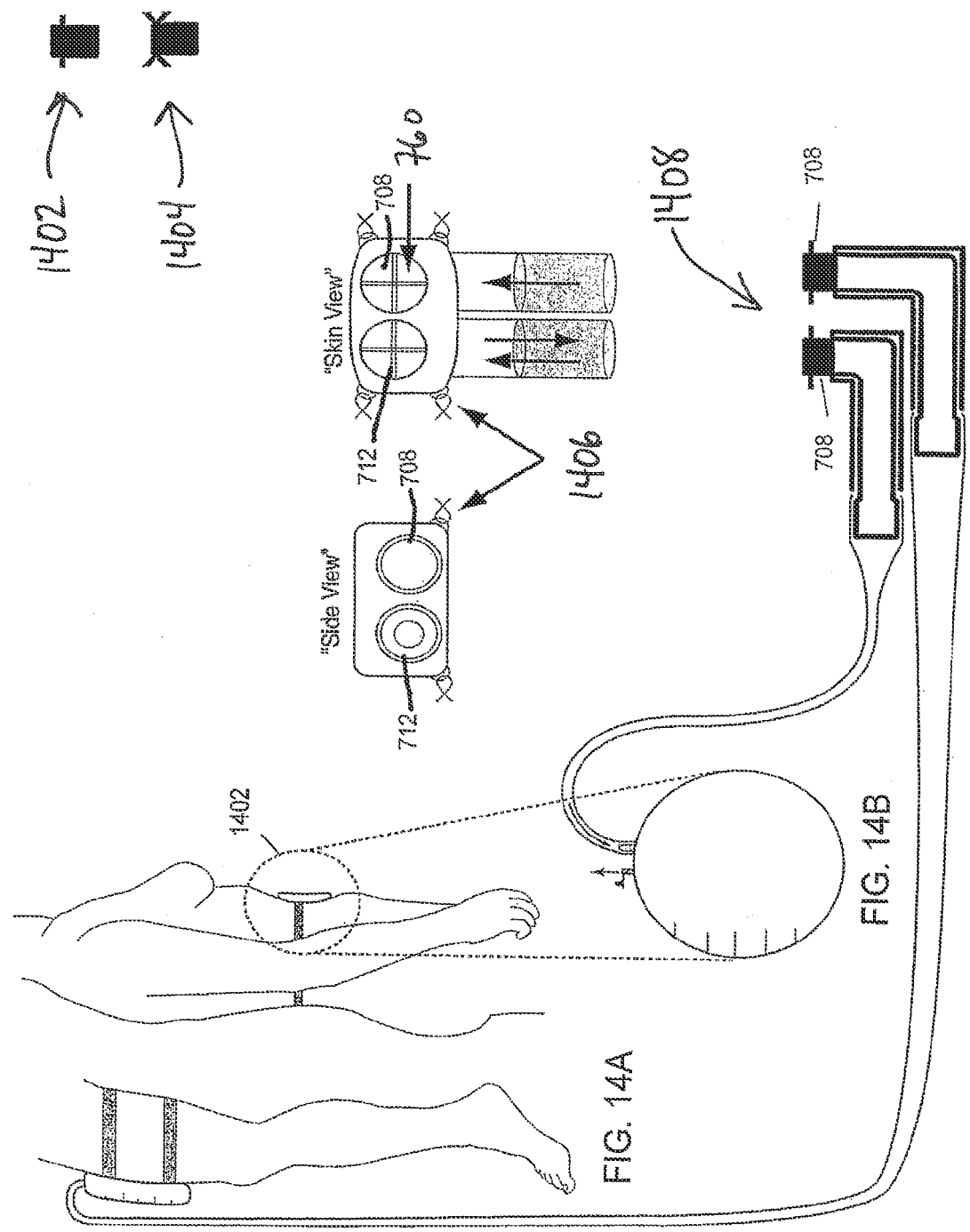

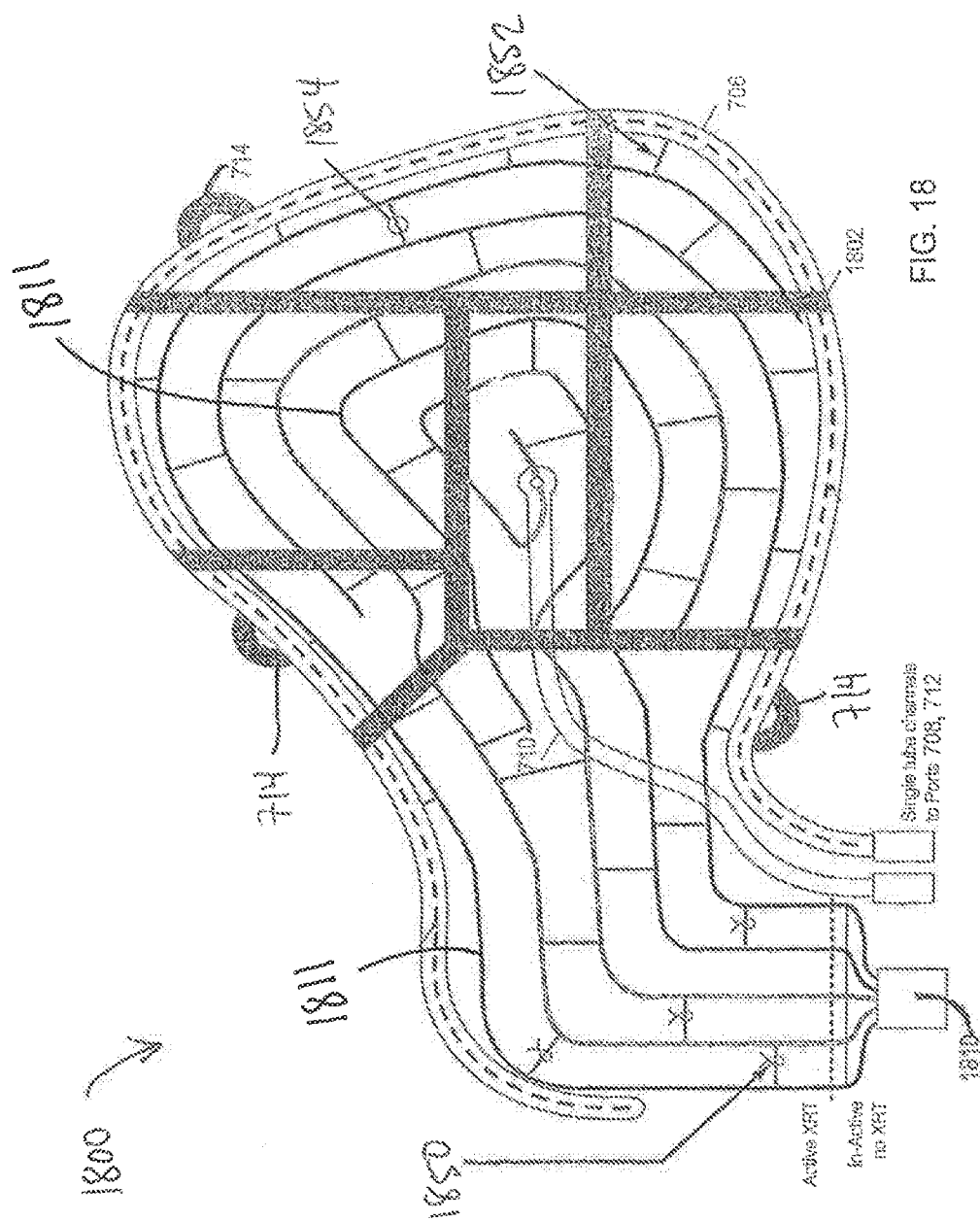

METHODS AND SYSTEMS FOR BREAST RECONSTRUCTION

CROSS-REFERENCE TO RELATED APPLICATIONS

This application is a continuation of U.S. patent application Ser. No. 13/220,426, filed Aug. 29, 2011, entitled "Methods and Systems for Breast Reconstruction", which is a continuation of U.S. patent application Ser. No. 12/063, 403 filed Jul. 9, 2008, now U.S. Pat. No. 8,080,057, issued Dec. 20, 2011, entitled "Methods and Devices For Breast Reconstruction", which is a U.S. National Stage under 35 U.S.C. §371 of International Patent Application No. PCT/US2006/031091, filed Aug. 9, 2006, which claims priority to U.S. Provisional Patent Application No. 60/706,543 filed Aug. 9, 2005, and U.S. Provisional Patent Application No. 60/737,657 filed Nov. 17, 2005, all of which are hereby incorporated in their entirety.

STATEMENT REGARDING FEDERALLY SPONSORED RESEARCH DEVELOPMENT

Not applicable

BACKGROUND OF THE INVENTION

1. Field of the Invention

The present invention relates to breast reconstruction, more particularly, to techniques for preserving the breast skin envelope for breast reconstruction.

2. Description of Related Art

For breast cancer patients who undergo mastectomies and desire breast reconstruction, reconstructive surgery generally occurs soon after the mastectomy, if not immediately after the mastectomy, to permit the best aesthetic outcomes. For patients with early-stage breast cancer, either stage 1 or stage 2 breast cancer, immediate reconstruction is feasible because these patients do not generally require post-operative radiation therapy. However, if the need for post-mastectomy treatment arises after the breast is reconstructed, the patient may be at an increased risk for complications, such as adverse aesthetic results and inhomogeneous radiation delivery. For example, as noted in many trials, survival advantages with post-mastectomy treatment occur when the internal mammary nodes are included within the radiation fields. To treat these internal mammary nodes while minimizing the dose to the heart and lungs, a separate electron beam on the medial chest wall is required to match the laterally placed opposed tangent fields. However, the sloping contour of a reconstructed breast leads to an imprecise geometric matching of the fields, and thus results in either exclusion of treatment to the internal mammary nodes and/or increased radiation of normal tissues. Additionally, the radiation may increase the chances of capsular contracture with an implant-based reconstruction, which can distort the appearance of the reconstructed breast and cause chronic chest wall pain and tightness among other issues. Autologous tissue can also be adversely affected by radiation treatments resulting in the necrosis of tissue that can result in complications and asymmetry with the constructed breast. Any surgical revisions to a radiated breast reconstruction can be unpredictable and cause multiple complications, as well as require multiple steps.

In recent trials, such as Danish and Vancouver Trials, results show that for patients with early-stage breast cancer, post-mastectomy radiation therapy in addition to chemotherapy reduces the rate of locoregional recurrences and increases survival rates. Unfortunately, the need for post-mastectomy radiation therapy cannot be reliably determined at the time of a mastectomy. Pathology analysis of the mastectomy specimen and nodal tissue on permanent sections removed during a mastectomy is performed before a decision of whether a patient needs post-operative treatments can be made, with results taking upwards of a week to return. This delay may cause reconstruction to be pushed back, affecting aesthetic outcomes for reconstruction. For example, for standard delayed reconstruction, if the breast skin is not completely removed, any remaining skin may be undesirable because the skin malleability or elasticity deteriorates during the waiting period and/or during any post-operative therapy. Any subsequent reconstruction will be less than desirable, causing physical, emotional, and physiological distress to the patient.

Currently, different devices are being used to prepare the breast area for a permanent implant. One example is a tissue expander, which typically includes a bladder or envelope that will hold a liquid such as saline. The tissue expander can be used to stretch any skin remaining from the mastectomy to a larger dimension, particularly to a dimension that can accommodate the breast implant. In order to stretch the skin, after the mastectomy, the tissue expander is implanted under tissue, such as under the muscles below a surgically removed breast. Prior to the placement of the permanent breast implant, a small amount of saline is added to the envelope periodically until a desired size is reached. Typically, by adding the liquid slowly over a period of weeks or months, the covering tissue is allowed to expand to accommodate the liquid. Alternatively, the bladder may be completely filled intraoperatively.

One problem with using tissue expanders after a mastectomy is the stretching of the tissue and/or the skin. Due to the removal of most tissue and/or skin in the breast area during the mastectomy, any remaining tissue and/or the skin can be stretched thin enough that damages such as tearing or protrusion of the tissue expander and/or an implant through the skin can occur. The surface, therefore, becomes too delicate and hard to work with during reconstruction.

If pathology results show that a patient requires post-mastectomy radiation therapy and/or chemotherapy, the tissue expanders may need to be removed to optimize treatment. For example, among other issues, if the inflated tissue expander remains on the chest wall, the tissue expander may deflect radiation beams, causing an inhomogeneous radiation field that exposes areas not needing therapy or not treating the regions that require treatment. Also, the tissue expander may be damaged due to the radiation beam, and thus may leak or otherwise lead to undesirable results. Subsequently, the tissue expander may need to be removed in order to proceed with post-mastectomy therapy (i.e., radiation therapy).

Alternatively, if a patient requires post-mastectomy radiation therapy, the liquid in the tissue expander may be removed prior to the treatment. This method cuts down the recovery time for the patient and may avoid delays in the start of post-mastectomy therapies. Generally, to deflate the tissue expander, a needle is inserted into a metal port integrated into the envelope of the tissue expander to draw out the liquid. However, there are complications caused by the metal port used to fill and drain the envelope. If a patient requires post-mastectomy radiation therapy and the tissue expander remains in the patient, the metal port can deflect the radiation beam, resulting in an inhomogeneous radiation field. Areas not needing radiation therapy may be exposed and can cause more harm to the patient, and areas needing treatment may not receive the radiation.

Another problem associated with current tissue expanders is when they are deflated, the bladder of the tissue expander curls in at the edges, creating a cupped profile. These cupped edges can deflect radiation beams. These edges may also cause pressure to the overlying skin and cause the skin to become irritated and/or cause the tissue expander to become exposed or protrude through the skin. Further, the backward pressure created by the expansion can push against the chest wall, creating a concave deformity on the surface on the chest wall. This can result in discomfort to the patient, including, but not limited to, pain and breathing problems. Upon reconstruction, the concave nature of the chest wall can create aesthetic problems, e.g., requiring more tissue to fill the space. This problem may create an unnatural breast shape and asymmetry with the contralateral breast.

Other problems associated with current tissue expanders include the deficiencies of removing fluids that collect at the expander after removal of the surgical drain, such as, for example, seroma fluids collecting at or around the breast region. Generally, patients would be required to undergo needle drainage and the use of an external catheter. The insertion of the needle may require radiographic imaging to avoid inadvertent puncturing of the expander. Additionally, the long-term use of the drainage catheter may cause a great risk of infection to the patient. As such, the inadvertent collection of peri-expander fluid in the breast and axillary area can be costly, cause significant complications, and can be inconvenient for the patient.

Any shortcoming mentioned above is not intended to be exhaustive, but rather is among many that tends to impair the effectiveness of previously known techniques for breast reconstruction; however, shortcomings mentioned here are sufficient to demonstrate that the methodologies appearing in the art have not been satisfactory and that a significant need exists for the techniques described and claimed in this disclosure.

SUMMARY OF THE INVENTION

The present disclosure provides methods and apparatuses for optimizing breast reconstruction for breast cancer patients or patients who undergo preventive mastectomies. The present disclosure provides a prosthesis that can be used to preserve the breast skin envelope and natural landmarks of the breast during a time period between the mastectomy and the definitive breast reconstruction for determining if any post-mastectomy therapy treatment is needed. Alternatively, the present disclosure provides a prosthesis that can be used to preserve the breast skin envelope and natural landmarks of the breast during a time period between the mastectomy and the definitive breast reconstruction for a patient to recovery from the mastectomy.

Additionally, the present disclosure provides methods and apparatuses that can optimize radiation treatments for patients who require post-mastectomy radiation therapy. In one embodiment, the prosthesis disclosed can remain in the breast cavity during conventional external beam radiation techniques. Alternatively, the prosthesis may be used to provide internal radiation techniques.

In one respect, a method is provided. The method involves performing a mastectomy on a breast and preserving a breast skin envelope. The mastectomy may be performed on patients with stage-I or stage-II breast cancer. The mastectomy may be performed on patients with stage-III or stage-IV breast cancer. Alternatively, the mastectomy may be performed on patients undergoing preventive mastectomies.

The method also includes removing a tissue sample, including, but not limited to, breast and nodal tissues, during the mastectomy for pathology analysis. The analysis may determine if post-mastectomy therapy, such as chemotherapy or radiation therapy is needed. During the analysis of the tissue sample, a breast skin preserver may be inserted into the breast and inflated. The preserver may be inflated with a liquid, gas, air, radiation material including liquid radiation material, soluble gases, dissolvable liquids or other radioisotopes that may be used for internal radiation treatment to a volume for preserving the breast skin envelope until at least the final results of the pathology reports are known.

In some respects, the preserver may include: a base structure configured to collapse during the inflation of the preserver, a balloon coupled to the base, where the balloon is inflated to a volume for preserving the breast skin envelope, an instillation/evacuation tube coupled to the balloon for inflating the balloon, and an instillation/evacuation port coupled to the instillation/evacuation tube In one embodiment, a needle locking system may be also be provided and may be used to access the instillation/evacuation port externally, where the port may be located underneath the skin.

Upon receiving results from the pathology analysis, the method includes a step for determining a time for breast reconstruction based on the pathology analysis. In some respects, the pathology report may recommend that a patient does not require post-mastectomy radiation treatment, and therefore, definitive breast reconstruction may be scheduled after the patient heals from the mastectomy surgery. In other respects, the pathology analysis may recommend the patient undergo post-mastectomy therapy, including, without limitation, chemotherapy and/or radiation therapy. As such, the breast reconstruction may be delayed until after the treatment is completed.

In one respect, prior to administering the post-mastectomy therapy, the preserver may be deflated. Alternatively, the preserver may remain inflated and a radioactive source may be provided to the preserver. The radioactive source may include, for example, at least one brachycatheter rod that emits radiation fields (i.e., limited field radiation therapy) to treat the chest wall underlying the skin preserver and nodal basins (e.g., axillary nodal basin and the like). Alternatively, the radioactive source may be a radioactive seed, delivered by, for example, a computer through a port of the prosthesis. The seed may be delivered to the base of the prosthesis or into an inflated or deflated balloon of the prosthesis.

In other respects, the step of administering the post-mastectomy therapy includes using at least brachycatheter rod emitting radiation fields internally and an external beam radiation technique to treat the skin and other nodal basin, via a radiation brassiere worn by a patient. The prosthesis may remain inflated for this embodiment. Alternatively, the prosthesis may be deflated.

In other respects, a method including performing a mastectomy on a breast and preserving a breast skin envelope may be provided. From the mastectomy, a tissue sample, including, but not limited to, breast and nodal tissues, may be removed for pathology analysis. A preserver may be inserted into the breast and inflated to a volume for preserving the breast skin envelope as well as other landmarks of the breast.

In one embodiment, the preserver includes, among other features, a base, a balloon coupled to the base, where the balloon is inflated to the volume for preserving the breast skin envelope, at least one instillation/evacuation tube coupled to the balloon for inflating/deflating the balloon, an instillation/evacuation port coupled to the instillation/evacuation tube, and a needle locking system coupled to the port. In one embodiment, the needle locking system may be used to access the port externally, where the port may be located underneath the skin.

Upon receiving results from the pathology, analysis requiring post-mastectomy cancer therapy treatment, the preserver may be deflated. Alternatively, the preserver remains inflated and at least one brachycatheter rod may be inserted into the base structure of the preserver. The at least one brachycatheter rod can administer internal radiation to treat, for example, the chest wall and axillary nodal basins.

In some embodiments, a combination of an external beam radiation and internal radiation via the at least one brachycatheter rod may be used. The combination radiation treatment may treat, for example, the breast skin, the chest wall, and internal nodal basins. Alternatively, only an external beam radiation may be administered.

After the step of administering a post-mastectomy treatment, the patient may undergo a breast reconstruction. Such steps including, without limitation, reinflating the prosthesis if the preserver was deflated for the treatment and removing the preserver prior to the breast reconstruction may be performed.

In other respects, a method for treating cancer in the chest area is provided. The method includes inserting a breast skin preserver into the breast and inflating the breast skin preserver. The preserver may be inflated to a volume for preserving the breast skin envelope until at least the final results of the pathology reports are known. The preserver may also be used to treat the internal chest area. The preserver may include: a base structure, a balloon coupled to the base, where the balloon is inflated to the volume for preserving the breast skin envelope, an instillation/evacuation tube coupled to the balloon for inflating the balloon, an instillation/evacuation port coupled to the instillation/evacuation tube, and a needle locking system coupled to the instillation/evacuation port. In one embodiment, the needle locking system may be used to access the port externally, where the instillation/evacuation port may be located underneath the skin.

The method also includes using a radiation brassiere to treat the external chest area. In one respect, the radiation brassiere may be used for patients who have undergone surgery. Alternatively, the radiation brassiere may be used for non-surgical patients. The radiation brassiere may include a plurality of panels adapted to receive radiation rods, the rods administering radiation treatment.

The term "prosthesis" or "preserver" as defined and used in this disclosure refers to a device that may be implanted into a patient, where the prosthesis/preserver may preserve the breast skin envelope, the breast dimensions, and other natural landmarks of the breast. In one respect, the prosthesis or preserver may be used to maintain the breast skin envelope and natural landmarks of the breast after a mastectomy and prior to breast reconstruction surgery (with or without post-mastectomy radiation therapy). Alternatively, the prosthesis or preserver may be used for patients with partial or breast defects or no surgical breast defects. The term prosthesis and preserver may be used interchangeably throughout the disclosure.

The terms "a" and "an" are defined as one or more unless this disclosure explicitly requires otherwise.

The term "substantially" or "about" and its variations are defined as being largely but not necessarily wholly what is specified as understood by one of ordinary skill in the art, and in one non-limiting embodiment the term substantially refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are openended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "coupled," as used herein, is defined as connected, although not necessarily directly, and not necessarily mechanically.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The figures are examples only. They do not limit the scope of the invention.

FIG. 7 is cross-sectional view of an external irradiation prosthesis including a plurality of ports, in accordance with embodiments of this disclosure.

FIGS. 8A-8C show the input and output tubes of a prosthesis for inflating and deflating the prosthesis, in accordance with embodiments of this disclosure.

FIG. 9 shows a built-in drainage system, in accordance with embodiments of this disclosure.

FIG. 10A shows a port of a prosthesis, in accordance with embodiments of this disclosure.

FIG. 10B shows a plurality of needles for a needle locking system that can be used with the port of FIG. 10A, in accordance with embodiments of this disclosure.

FIG. 11A shows a 3-port and connection design, in accordance with embodiments of this disclosure.

FIG. 11B shows a 2-port and connection design, in accordance with embodiments of this disclosure.

FIGS. 13A and 3B show a syringe-loaded unclogger, in accordance with embodiments of this disclosure.

FIG. 14A shows a gravity drainage system, in accordance with embodiments of this disclosure.

FIG. 14B shows a flat suction bulb drainage system, in accordance with embodiments of this disclosure.

FIG. 18 is cross-sectional view of a brachytherapy irradiation prosthesis including a plurality of ports, in accordance with embodiments of this disclosure.

DESCRIPTION OF ILLUSTRATIVE EMBODIMENTS

Figure 1:
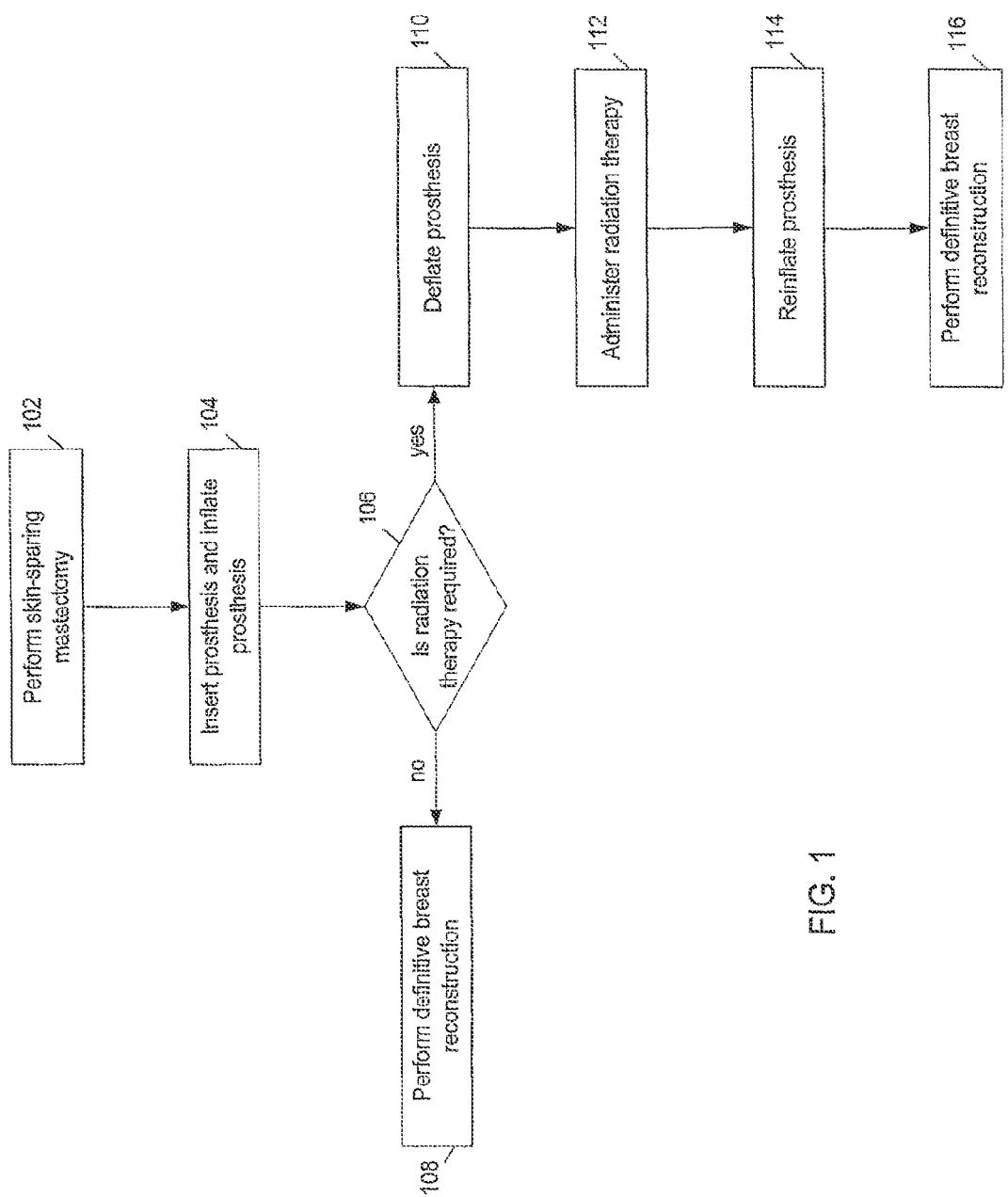
FIG. 1 is a flowchart showing steps of a method for delayed-immediate breast reconstruction, in accordance with embodiments of this disclosure.

The present disclosure provides techniques for breast reconstruction in patients who go through at least one mastectomy due to the presence of breast cancer and/or patients who go through at least one preventive mastectomy due to elevated risks to develop breast cancer. By using the disclosed prosthesis and/or radiation brassiere, which preserves the shape and form of the breast skin envelope after a skin-sparing mastectomy and which does not substantially interfere with any post-operative therapies, patients can obtain a more natural, aesthetically pleasing outcome after breast reconstruction surgery. Additionally, the prosthesis provides for optimal radiation treatments for patients requiring post-mastectomy treatments.

In particular, the present disclosure provides techniques for preserving the breast skin and other natural landmarks of a breast after a mastectomy and prior to a definitive reconstructive surgery. Between the time of the mastectomy and reconstructive surgery, the method may include a post-mastectomy treatment and/or may include time for a patient to heal from the mastectomy.

In one respect, a prosthesis, such as the external beam prosthesis or the brachytherapy prosthesis may be inserted into a breast. The prosthesis may be inflated up until for example, post-mastectomy treatment (e.g., external or internal radiation treatments) or until a definitive reconstructive surgery (with or without a post-mastectomy treatment).

Additionally, the present disclosure integrates the breast reconstruction stage together with post-mastectomy radiation treatments. For example, the present disclosure provides a prosthesis that may be suitable with external beam radiation techniques (e.g., external beam prosthesis). Similarly, the present disclosure provides a prosthesis configured to receive a radiation source (e.g., radiation rods, radioactive seeds, radioactive liquids or gases, etc.) that may be implanted into a patient for internal radiation treatment (e.g., brachytherapy prosthesis). Alternatively or in addition to the above mentioned prosthesis, a radiation brassiere may be used. The radiation brassiere may provide, amongst other things, an external radiation treatment of the breast area for patient requiring post-mastectomy treatments.

It is noted that the one of ordinary skill in the art would recognize that the prosthesis and radiation brassiere may be used independently from each other or in combination with one another as well with other devices of the present disclosure. For example, a patient may receive a prosthesis used for to preserve the breast skin envelope and other landmarks (delayed-immediate patients), or a prosthesis with radiation ports for brachytherapy treatment may be used, or a radiation bra. Alternatively, a patient may receive a combination of the devices including, for example, a prosthesis without radiation port (i.e., external beam prosthesis) and a radiation brassiere. Further, a patient may receive a prosthesis with radiation port(s) for internal radiation treatment as well as receive external beam radiation (with or without a radiation brassiere).

In addition to discussing the techniques for breast reconstruction using the disclosed prosthesis, the present disclosure considers methods for patients with different stages of breast cancer. In one embodiment, patients with advanced stages of breast cancer, who were generally not candidates for breast reconstruction, may now have the option for breast reconstruction after post-mastectomy treatments. As such, in some embodiments, methods for reconstruction are provided for patients who undergo mastectomies and are required to have post-mastectomy therapy, e.g., patients with stage-III breast cancer or stage-IV breast cancer. Therefore, the method discusses steps to prepare a field, e.g., the breast area for a delayed reconstruction. This method is referred to as a delayed-delayed breast reconstruction in this disclosure.

In other embodiments, methods for reconstruction are provided for patients, who undergo mastectomies and are at risk for post-mastectomy therapy, e.g., patients with stage-1 or stage-2 breast cancer. These patients may not know whether they will require therapy until after the mastectomy is performed and a pathology report is issued. This may be due to the inability to identify things such as, but not limited to, micrometastases, the size of an invasive tumor in breast parenchyma, and the like. Therefore, the methods of the present disclosure provide steps to prepare a field, e.g., the breast area for a possible immediate breast reconstruction after pathology reports are available. In some embodiments, the patient may require radiation therapy and as such, may require reconstruction after the treatment is completed. This method is referred to as a delayed-immediate breast reconstruction in this disclosure.

Similarly, for patients who undergo a mastectomy due to breast cancer in one breast and preventive mastectomy in the other, the present disclosure discusses methods for a more natural, aesthetically pleasing reconstruction. These patients may be a delayed-immediate breast reconstruction candidate or a delayed-delayed breast reconstruction candidate. The process may depend on the type of breast cancer and/or the risk level of a patient.

Delayed-Immediate Breast Reconstruction

For patients with carcinoma in-situ or early-stage breast cancer (stage-1 or stage-2 breast cancer) who undergo mastectomies, immediate reconstruction offers the best aesthetic outcome if post-mastectomy radiation is not required. If post-mastectomy therapy may be required, delaying definitive breast reconstruction can avoid aesthetic and problems associated with radiation delivery that can occur after an immediate breast reconstruction. Generally, post-mastectomy radiation therapy recommendations do not occur before or even during a mastectomy. Most recommendations come after a review of permanent tissue samples, which can take several weeks. As such, to optimize reconstruction, a multiple step approach may be used, such as the non-limiting example shown in FIGS. 1 and 2. In one embodiment, a patient may undergo a skin-sparing mastectomy where the breast skin envelope is substantially preserved (step 102). In order for the patient to recover from the mastectomy and in order to determine if a patient requires post-operative treatment, a prosthesis may be inserted to substantially preserve the breast skin and landmarks of the breast. In one embodiment, a prosthesis, which may be deflated during the insertion into the breast cavity, may be filled with a liquid intraoperatively or post-operatively such that the 3-D shape of the breast skin envelope is maintained (step 104). Particularly, the prosthesis may preserve the shape and important landmarks of the breast, such as, but not limited to, the inframammary fold of the breast until definitive breast reconstruction is performed. The prosthesis is discussed in further details below.

In step 106, depending on a result of a pathology report, a patient may or may not be required to undergo post-mastectomy radiation therapy. For patients that do not require post-mastectomy radiation treatment, a definitive breast reconstruction may be performed within several weeks of the mastectomy using the preserved skin breast envelope (step 108). This time frame may avoid any delays in the start of adjuvant chemotherapy (if needed) and avoids capsule formation (e.g., an internal scar around the prosthesis) to retain the malleability of the breast skin envelope.

For patients who require radiation therapy, a series of steps, such as steps 110, 112, 114, and 116 may be performed. In one embodiment, the time period between the mastectomy and the start of treatment allows for an internal scar (capsule formation) to form around the prosthesis prior to a possible step of deflation. The formation creates a large space within the scar capsule prior to a possible step of deflation, which allows for reinflation to occur after radiation treatment despite the associated inflammatory effects of radiation. In some embodiments, referring to step 110, the fluid may be drained from the prosthesis, leaving a substantially deflated prosthesis, which may rest flat against the chest wall. The drainage of the fluids leaving may allow for treatment of internal mammary lymph nodes without excess delivery of radiation beams to the heart and lungs. A deflated prosthesis may also avoid an inhomogeneous dose distribution.

The prosthesis, which remains in the breast cavity during radiation therapy (step 112), may maintain its structural integrity during the therapy, and thus, may be used to prepare the breast cavity for reconstructive surgery. Additionally, the prosthesis does not interfere with the treatment, and thus, is more effective than conventional techniques. A more detailed description of the prosthesis is discussed below.

After radiation therapy is completed, the prosthesis may be reinflated (step 114). In some embodiments, reinflation occurs several weeks after radiation therapy has completed to allow the resolution of any radiation induced skin desquamation, which reduces the risk for infection. The reinflation step may include gradually reinflating the prosthesis with a fluid over a period of time. For example, approximately every few weeks, a small amount of air, saline or other suitable liquids may be added into the prosthesis, allowing for the prosthesis to regain the domain of the breast cavity achieved prior to deflation (step 110) and the start of radiation treatment (step 112). After the reinflation time period, the volume of the prosthesis is similar to or substantially equal to the volume of the prosthesis during the inflation step (step 104). Once the prosthesis is reinflated, the patient may undergo definitive breast reconstruction (step 116). In one embodiment, step 116 may include removing the prosthesis. Once the prosthesis is removed, techniques known in the art including, without limitation, transverse rectus abdominis musculocutaneous (TRAM) flaps, superior gluteal artery perforator (SGAP) flap, deep inferior epigastric perforator (DIEP) flap, latissimus dorsi (LD) flap plus implant, and the like may be used to reconstruct the breast.

Figure 2:
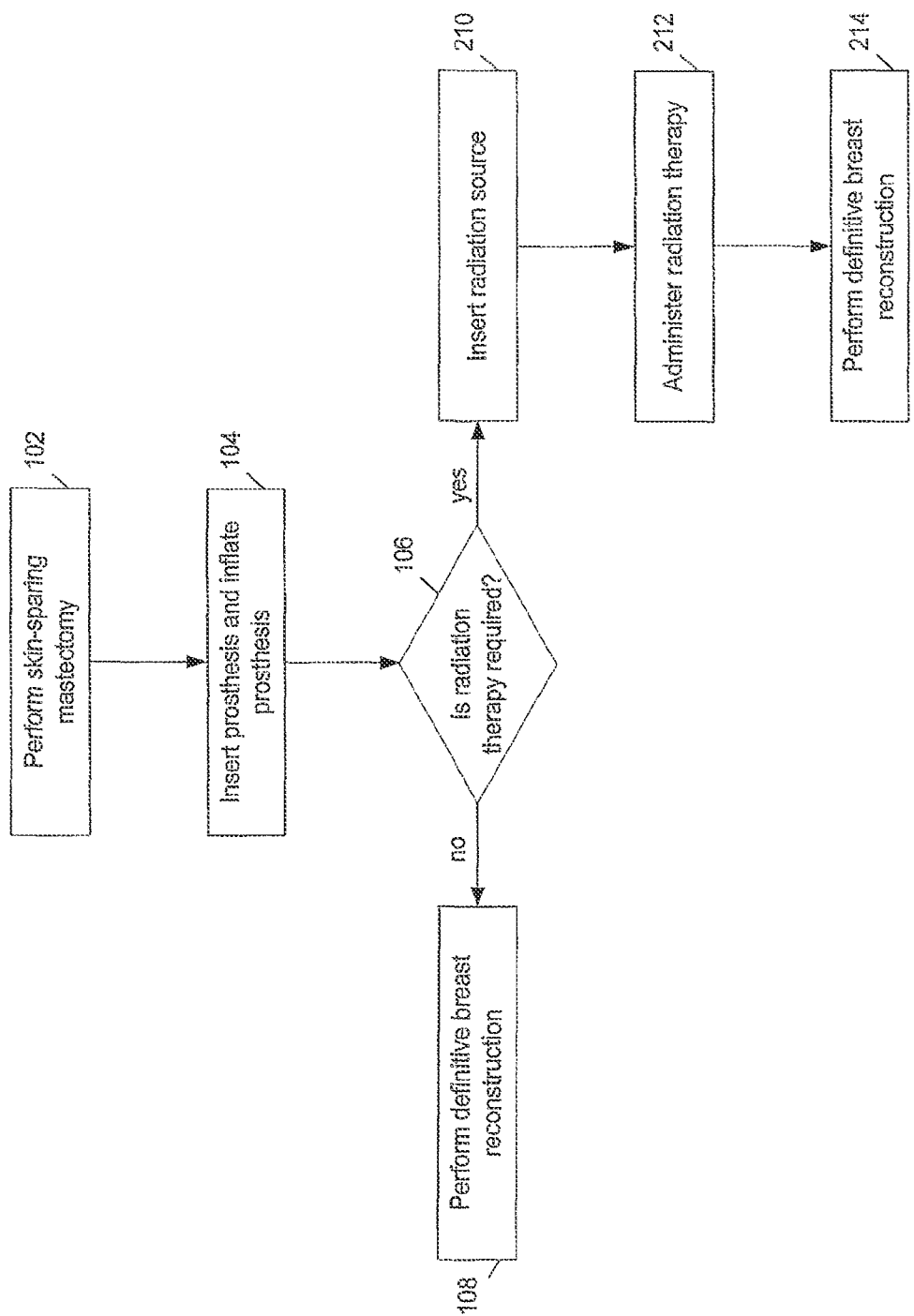
FIG. 2 is a flowchart showing steps of a method for delayed-immediate breast reconstruction, in accordance with embodiments of this disclosure.

Alternatively, in other embodiments, a patient who requires post-mastectomy radiation therapy in step 106 may undergo a brachytherapy radiation process, as shown in FIG. 2. Steps 102, 104, 106, and 108 are similar to those shown in FIG. 1. In step 210, without deflating the prosthesis, at least one brachytherapy may be administered. In one respect, a radiation source such as, but not limited to, at least one radiation rod may be inserted into sleeves built into the prosthesis. The radiation rod(s), positioned on the chest wall and axillary region may administer radiation emissions (step 212). In combination with the radiation rods, the radiation therapy may also include external beam irradiation to the skin and other nodal basins. Upon completion of step 212, the radiation rods may be removed, and the patient may move ahead to other treatments or reconstruction prior to the removal of the prosthesis and may subsequently undergo a definitive breast reconstruction (step 214).

It is noted that other radioactive sources (e.g., seed, liquid, gaseous radioactive source) may be used in the brachytherapy radiation process. In some respect, the brachytherapy process may include more than one radioactive source used in combination to treat the patient.

Delayed-Delayed Breast Reconstruction

Patients with stage-3 or stage4 breast cancer (large primary advanced breast cancer or locally advanced breast cancer, LABC) generally have treatment recommendations that include a mastectomy and a post-mastectomy radiation therapy session. Up until now, these patients were not prime candidates of radiation delivery with breast reconstruction. This may be due to, among other issues, the problems associated with the conventional implants, i.e., the integrity of the implant during the post-mastectomy radiation therapy, and/or the inability to reconstruct a natural-looking breast due to the condition of the breast skin.

In addition, traditional mastectomy generally resects all breast skin for stage III patients, requiring a definite, complete 3 D reconstruction of the breast with significant autologous tissue requirements. If a traditional expander is placed after radiation therapy, certain complications can arise such as infection, poor wound healing, and protrusion of the implant through the breast skin. Further, adverse radiation effects on autologous tissue reconstruction in these patients may affect the final aesthetic results, leading to unnatural breast shape and asymmetry compared to the contralateral breast. This may lead to, among other issues, psychological distresses to the patient, especially since most autologous tissue can be lost and any revision surgery after radiation therapy resulting in a poor aesthetic outcome.

Figure 3:
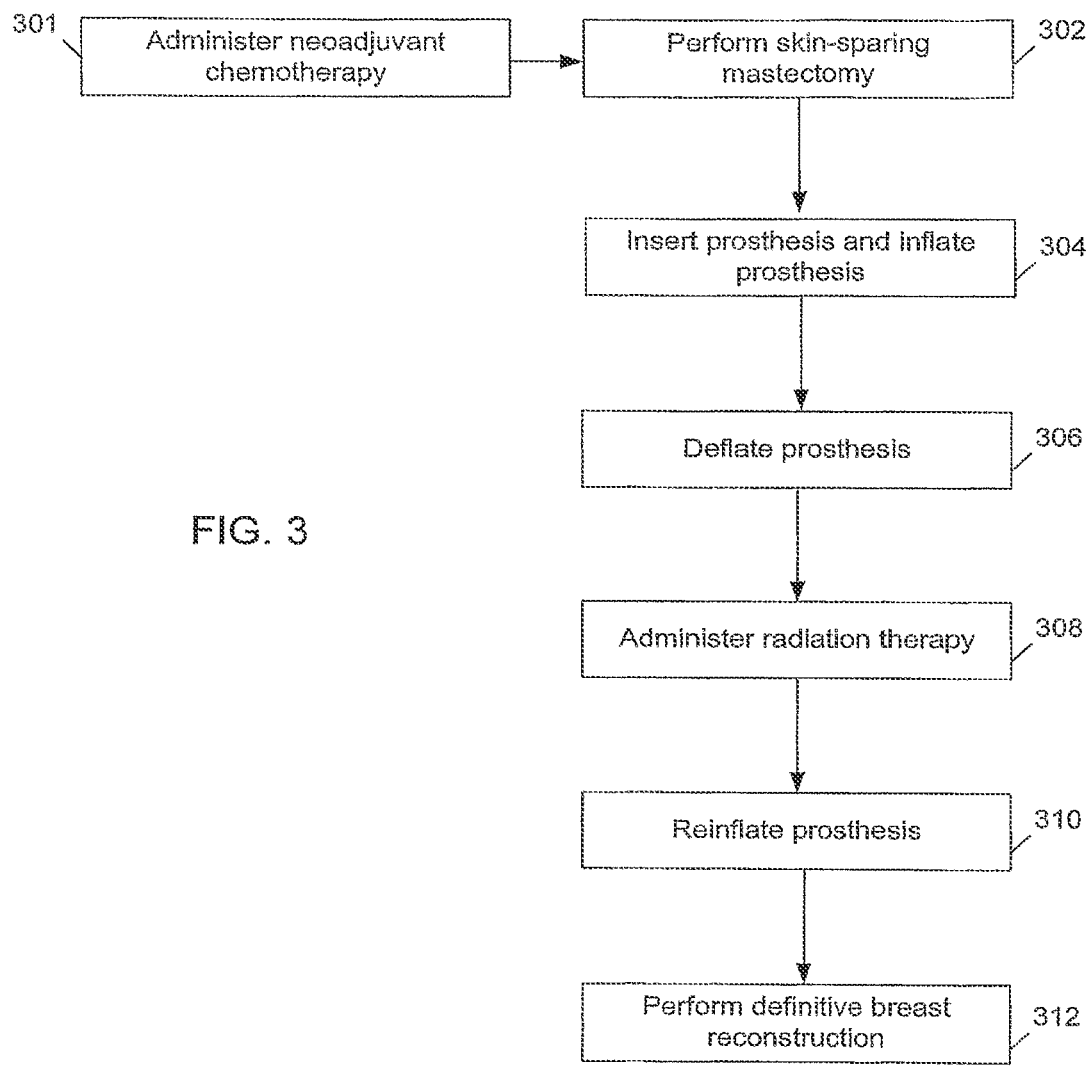
FIG. 3 is a flowchart showing steps of a method for delayed-delayed breast reconstruction, in accordance with embodiments of this disclosure.

Referring to FIG. 3, a method for optimizing treatment and aesthetic outcomes from breast reconstruction for patients with stage-3 breast cancer is shown. In one embodiment, patients may undergo a skin-sparing mastectomy (step 302), post-mastectomy radiation therapy (step 308), and a definitive breast reconstruction process (step 312). The mastectomy may include, for example, a skin-preserving mastectomy that retains the breast skin envelope.

In some embodiments, it may be necessary for a patient to undergo neoadjuvant chemotherapy session (step 301) prior to a mastectomy. The combination of the neoadjuvant chemotherapy, mastectomy, and post-operative therapy may further reduce the risk of recurrence as well as increase survival rates. Upon completion of the neoadjuvant chemotherapy, a patient may undergo a skin-sparing mastectomy, removing the breast tissue while preserving the breast skin envelope (step 302).

After the mastectomy, a patient may be allowed time to recover from the surgery. In some embodiments, the recovery time may be a few weeks upwards to a few months. As such, a prosthesis may be inserted into the breast cavity at the time of the mastectomy to preserve the breast skin envelope and other landmarks of the breast. In one embodiment, a deflated prosthesis may be inserted into the breast cavity (step 304). The prosthesis may then be inflated to a volume that preserves the 3-D shape and landmarks of the breast. In one embodiment, the prosthesis may be inflated in a gradual manner over time until a desired volume is achieved, i.e., post-operatively. Alternatively, the prosthesis may be filled to the desired volume in one step, i.e., intraoperatively. Embodiments of the inflation process will be discussed in more detail below.

When the patient is ready for radiation therapy, the prosthesis may be deflated (step 306). In one embodiment, if a fluid was used to inflate the prosthesis during step 304, the fluid may be drained using a port coupled to the prosthesis. Step 306 may continue until the prosthesis is completely drained and lies substantially flat against the chest wall. The deflation process of the prosthesis will be discussed in more detail below with respect to the remote port design and the external access to the prosthesis using a needle-locking system of the prosthesis. Upon the deflation of the prosthesis, a radiation therapy may be administered (step 308). In one embodiment, the patient may undergo an external beam irradiation technique or other radiation techniques known in the art.

After the radiation therapy, the breast area may be prepared for definitive reconstruction. In one embodiment, the prosthesis may be reinflated (step 310). In one embodiment, the prosthesis may be reinflated in a gradual manner, where a small amount of fluid (e.g., saline, water, distilled water, etc.) may be added to the prosthesis over a period of time. The prosthesis may be reinflated to a volume similar to or substantially equal to the volume achieved in step 304. This gradual inflation allows for the breast skin envelope to regain the 3-D shape of the breast and aids the skin to adjust to the volume.

Once the prosthesis is reinflated to a desired volume, the patient may undergo definitive breast reconstruction (312). In one embodiment, step 312 includes steps for removing the prosthesis. Once the prosthesis is removed, techniques known in the art including, without limitation, transverse rectus abdominis musculocutaneous (TRAM) flaps, superior gluteal artery perforator (SGAP) flap, deep inferior epigastric perforator (DIEP) flap, latissimus dorsi (LD) flap plus implant, and the like may be used to reconstruct the breast.

Figure 4:
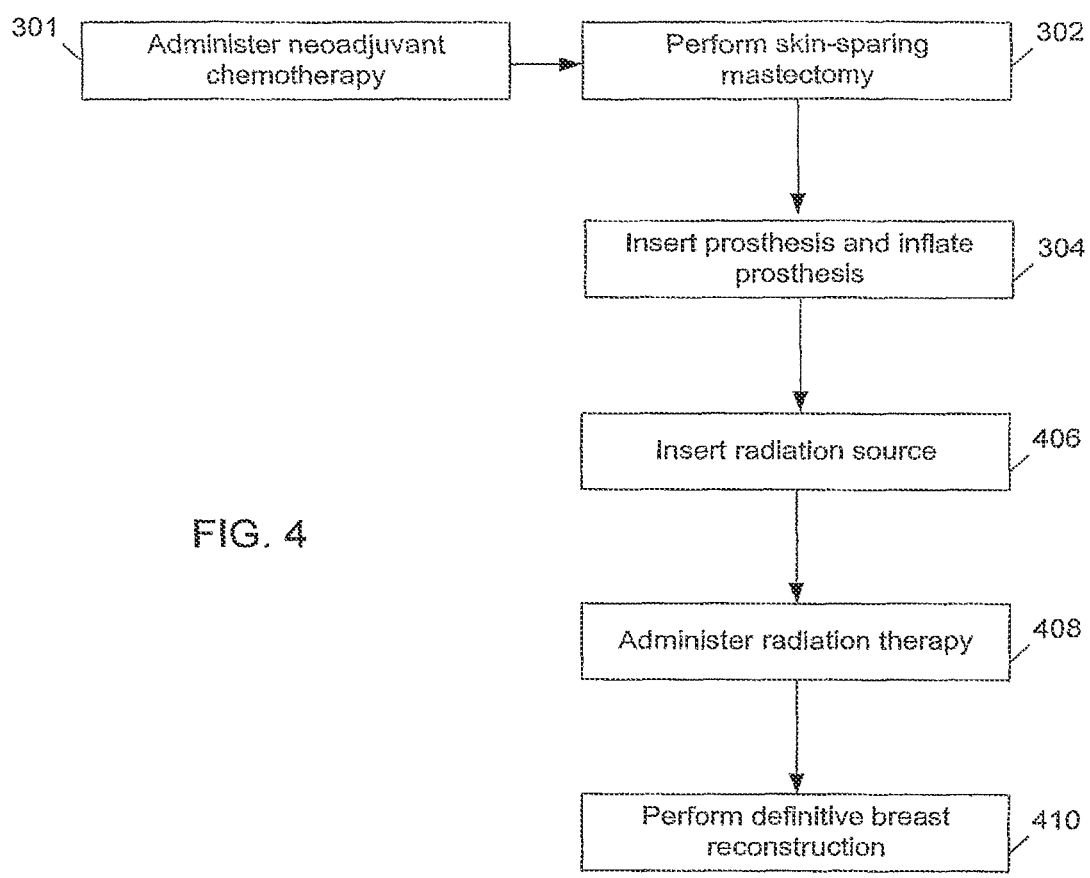
FIG. 4 is a flowchart showing steps of a method for delayed-delayed breast reconstruction, in accordance with embodiments of this disclosure.

In some embodiments, the step of administering a radiation therapy (e.g., step 308) may include an internal irradiation process. Referring to FIG. 4, techniques for a delayed-delayed breast reconstruction is shown. steps 301, 302, and 304 are similar to the steps of FIG. 3. After the patient has recovered from the mastectomy, or after the administering of post-mastectomy chemotherapy, and/or after the prosthesis has been inflated to a desired volume to maintain the shape and landmarks of the breast, a radioactive source, such as, but not limited to, radiation rods may be inserted into tracks built-into the prosthesis (step 406). The at least one brachycatheter rod may administer radiation emissions (step 408). Upon completion of the radiation therapy, the patient may undergo definitive breast reconstruction and any intermediate steps prior to reconstruction, including, without limitation, removing the brachycatheter rod, waiting for the patient to recover from the radiation therapy, administering other post-mastectomy treatments such as chemotherapy, etc., as shown in step 410.

Alternatively, step 406 may include providing other radioactive sources to the prosthesis. For example, a radioactive seed, a radioactive conducting wire, liquid or gaseous radiation sources may be used separately or in any combination for a radiation therapy. In one respect, the radioactive sources may be provided to tracks built-into the prosthesis. In addition to or alternatively, the radioactive source(s) may be provided to the inflated or deflated balloon of the prosthesis.

In other embodiments, step 408 may also include an external beam irradiation in combination with the internal irradiation technique. An external beam may irradiate the skin area and other nodal basins while the at least one brachycatheter rod integrated with the prosthesis delivers radiation to, for example, the chest wall and axillary and internal mammary nodal basins. Upon completion of the radiation therapy, the patient may undergo intermediate steps prior to reconstruction, including, without limitation, removing the brachycatheter rod, waiting for the patient to recover from the radiation therapy, administering of other post-mastectomy treatments such as chemotherapy, etc. A definitive breast reconstruction step may follow (step 410).

Preventive Mastectomies

For patients who are at high risk for breast cancer, preventive mastectomies may reduce the chances of occurrence in the breast cavity. In some cases, a preventive mastectomy can occur at the same time a breast with abnormal cells is removed. For these patients, who may or may not require post-mastectomy treatments, a delay in reconstructing the breast from the preventive mastectomy such that both breasts are reconstructed at the same time may reduce the healing process and improve the aesthetic outcome for the patient. For example, for patients with stage-1 or stage-2 breast cancer, the determination of post-mastectomy treatments may take weeks to determine. As such, preserving the breast skin envelope of the breast removed from the preventive mastectomy may be needed.

Alternatively, in other embodiments, the preventive mastectomy may be performed at the time of a definitive reconstruction of the breast removed due to abnormal cells. This allows for the breast removed from the preventive mastectomy to have immediate reconstruction, avoiding unnecessary scarring in this breast.

In one embodiment, a prosthesis may be inserted into the breast cavity of a breast removed for preventive measures. Similar to the step 104 in FIGS. 1 and 2 or step 304 of FIG. 3, the prosthesis may be inflated to a volume such that the 3-D shape and landmarks of the breast are maintained. If a patient does not require post-mastectomy treatment in the breast with abnormal cells, both breasts may be prepared for definitive reconstruction.

If a patient requires a post-mastectomy treatment, such as radiation in the breast cavity with abnormal cells, the prosthesis in the breast removed for preventive measures may remain inflated. Alternatively, the prosthesis in the breast removed for preventive measures may be deflated (similar to step 110 of FIG. 1 or step 306 of FIG. 3) during the duration of the post-mastectomy radiation. In this embodiment, after the post-mastectomy radiation, the prosthesis may be reinflated, similar to step 114 of FIG. 1 or step 310 of FIG. 3. The prosthesis may be reinflated in a gradual manner, where a predetermined amount of fluid may be inserted into the prosthesis at a predetermined interval. The insertion process may continue until the prosthesis attains a volume similar to or substantially equal to the volume achieved after the mastectomy and prior to the deflation step. Alternatively, the prosthesis may be inflated by adding, in one step, a fluid such that the volume of the prosthesis is to or substantially equal to the volume achieved after the mastectomy and prior to the deflation.

In other embodiments, patients who have a higher risk of getting breast cancer due to, for example, genetics, the removal of both breasts may reduce chances of occurrences. In one embodiment, a prosthesis may be inserted into each breast cavity after the mastectomy and inflated to maintain the shape and landmarks of breast skin envelope. The method allows for pathology analysis of the tissue sample to be determined before a definitive strategy for breast reconstruction to be decided.

Breast Skin Preserving Prosthesis

The prosthesis referred to in the flowcharts of FIGS. 1 through 4, is a breast preserving prosthesis that may preserve the shape, form, dimensions, and natural landmarks of the breast skin envelope after a skin-sparing mastectomy. The use of the prosthesis to prepare the breast area may aid in obtaining a more natural, aesthetically pleasing outcome after breast reconstruction surgery.

Additionally, the prosthesis may maintain its structural integrity during an irradiation process and may also not interfere with post-operative therapy. For example, the prosthesis may be manufactured from materials that would not deflect radiation beams. The prosthesis may also be manufactured in such a way that the materials would not degrade from the exposure to the radiation beams and will allow instillation of a radioactive material to treat surrounding tissues.

Figure 5A:
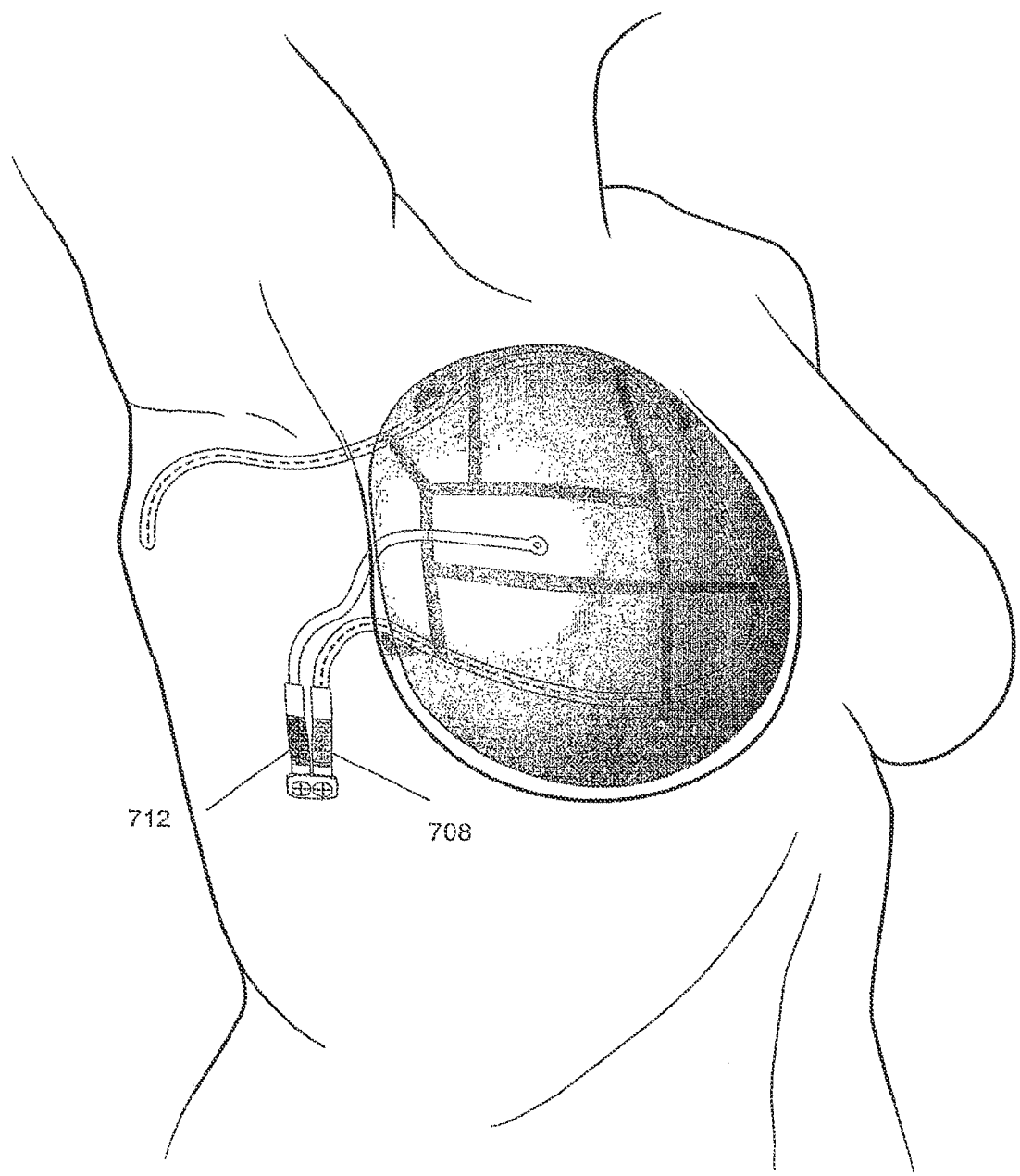
FIGS. 5A and 5B show an illustration of inflated external beam irradiation prosthesis and a brachycatheter radiation prosthesis, respectively, inserted into a breast cavity, in accordance with embodiments of this disclosure.
Figure 5B:
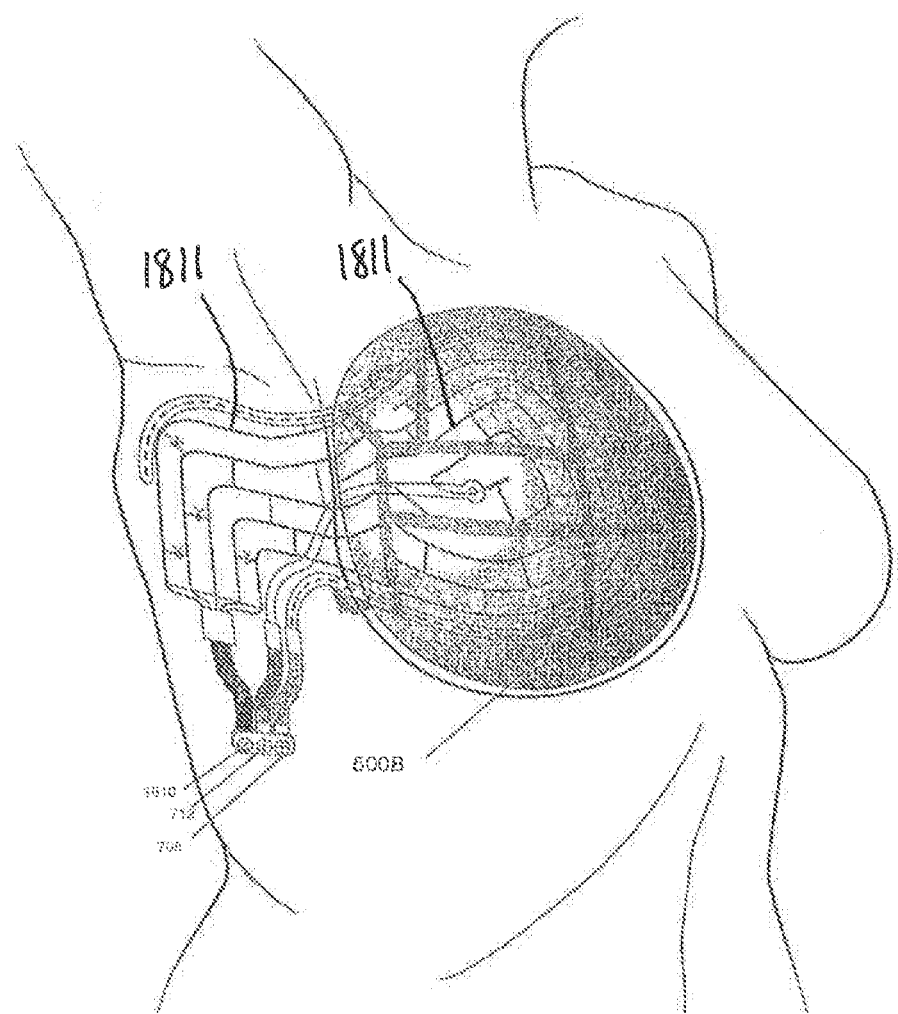
Figure 6A:
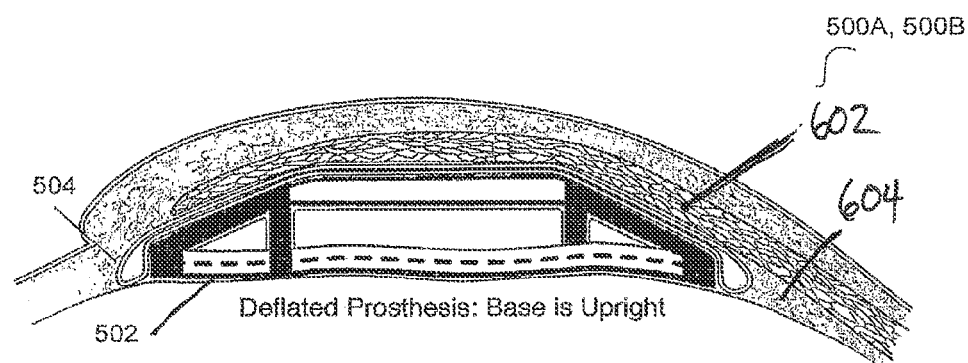
FIG. 6A is cross-sectional view of a deflated prosthesis, in accordance with embodiments of this disclosure.
Figure 6B:
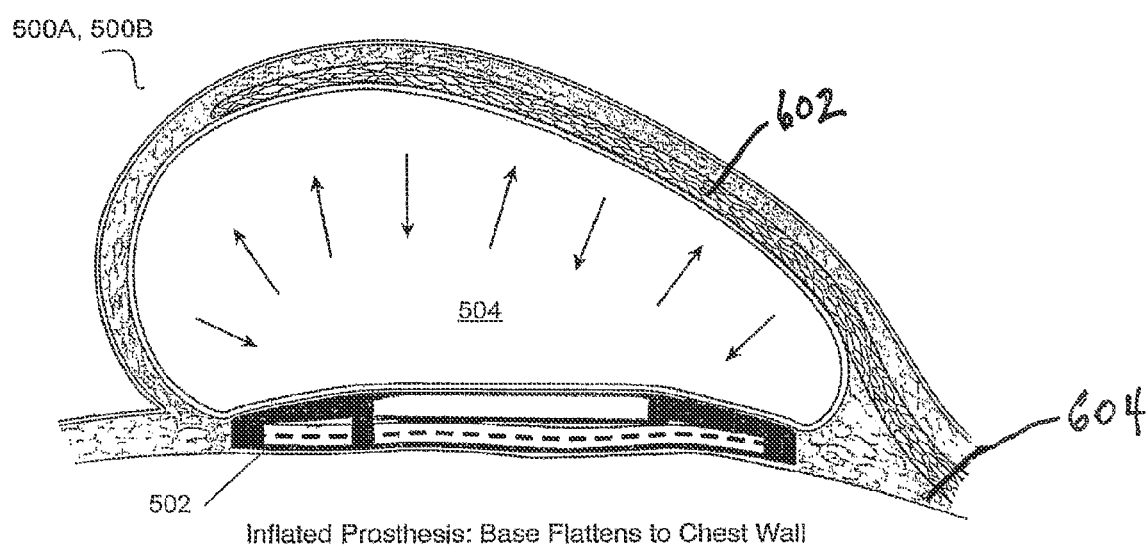
FIG. 6B is cross-sectional view of an inflated prosthesis, in accordance with embodiments of this disclosure.

For example, referring to FIGS. 5A and 5B, an external beam prosthesis (500A) and a brachytherapy prosthesis (500B) is shown, respectively, may be inserted into a breast cavity after a mastectomy, and may be inflated to a volume that may preserve the 3-D shape, form, and landmarks of the breast. In one embodiment, the volume of prosthesis 500A or 500B may be an amount such that the breast is similar to or substantially equal to the shape and size of the breast prior to the mastectomy. Alternatively, the volume may be an amount such that the breast is smaller or larger than the breast prior to the mastectomy. External beam prosthesis 500A and brachytherapy prosthesis 500B are discussed in further details below In one embodiment, prosthesis 500A or 500B may be inserted into a breast cavity and placed underneath the pectoralis major muscle 602 in a deflated state and on the chest wall 604, as shown in FIG. 6A (a cross section of prosthesis 500A or 500B on a chest wall). Prosthesis 500A or 500B may include base structure 502 coupled to balloon 504. In one embodiment, prosthesis 500A or 500B may comprise an outer shell that may be soft, yet durable. The flexible nature of the prosthesis avoids causing injury to the chest wall 604 and/or the breast skin during insertion, inflation, or reinflation, and during radiation. In other embodiments, prosthesis 500A or 500B may also be manufactured from materials that may allow optimal penetration of radiation beams, while avoiding divergence of the beam fields that may result in an inhomogeneous dose distribution.

In addition, prosthesis 500A or 500B may be made of a material that may maintain its structural integrity throughout the various steps (e.g., steps shown in FIGS. 1, 2, 3, and 4). For example, prosthesis 500A or 500B may be made of materials that may not breakdown into different byproducts that may lead to structural degradation.

When deflated, balloon 504 lies on base structure 502. The profile of balloon 504 does not include cupped edges and therefore, may not interfere with any potential post-mastectomy radiation treatments and does not injure the overlying skin, i.e., the prosthesis 500A or 500B does not protrude or is exposed through the skin. Additionally, base structure 502, may include a stable and spring-like framework and may be extended in an upright manner to reduce or substantially eliminate pressure on the chest wall 604 when balloon 504 is in an inflated state, preventing an indention in the chest wall 604 of the patient.

In one embodiment, when the prosthesis is deflated, for example, prior to radiation, the flexible, spring-like framework of base 502 may allow the prosthesis to maintain its structural integrity over contractile forces from radiation beams, as shown in FIG. 6A. Therefore, if the prosthesis was reinflated after the radiation therapy, the prosthesis may allow for optimal re-inflation, i.e., maintain the shape and volume of the breast prior to deflation.

In other embodiments, when the prosthesis is deflated, base 502 and balloon 504 may contour to the anterior chest wall, thus avoiding elevated and irregular edges. The profile of balloon 504 in the deflated state may not interfere with radiation delivery. Additionally, in the deflated state, the prosthesis does not sink or settle into the chest well 604, and thus, reduces or substantially eliminates the risk of creating a concavity in the chest wall 604.

When the prosthesis is inflated or reinflated (e.g., step 104 of FIGS. 1 and 2, step 304 of FIGS. 3 and 4, step 114 of FIG. 1, or step 310 of FIG. 3), balloon 504 may be injected with a fluid such as, but not limited to, saline, water, distilled water and the like. Alternatively, any biocompatible material may be used to inflate balloon 504. As a non limiting example, biocompatible materials such as hydrogel, collagen, fibrin, elastin, or the like may be injected into balloon 504. In other embodiments, balloon 504 may be injected with air. Alternatively, balloon 504 may be filled with a liquid, gaseous, or other suitable radioactive materials used for treatment of the breast cavity. The insertion of the radioactive material may accelerate breast irradiation.

In one embodiment when the prosthesis is inflated, the shape of balloon 504 and the base structure 502 may attain a more natural, ptotic shape breast skin envelope. The preservation of the breast skin is this configuration allows for a more aesthetically pleasing outcome when a definitive breast reconstruction is performed.

Figure 6C:
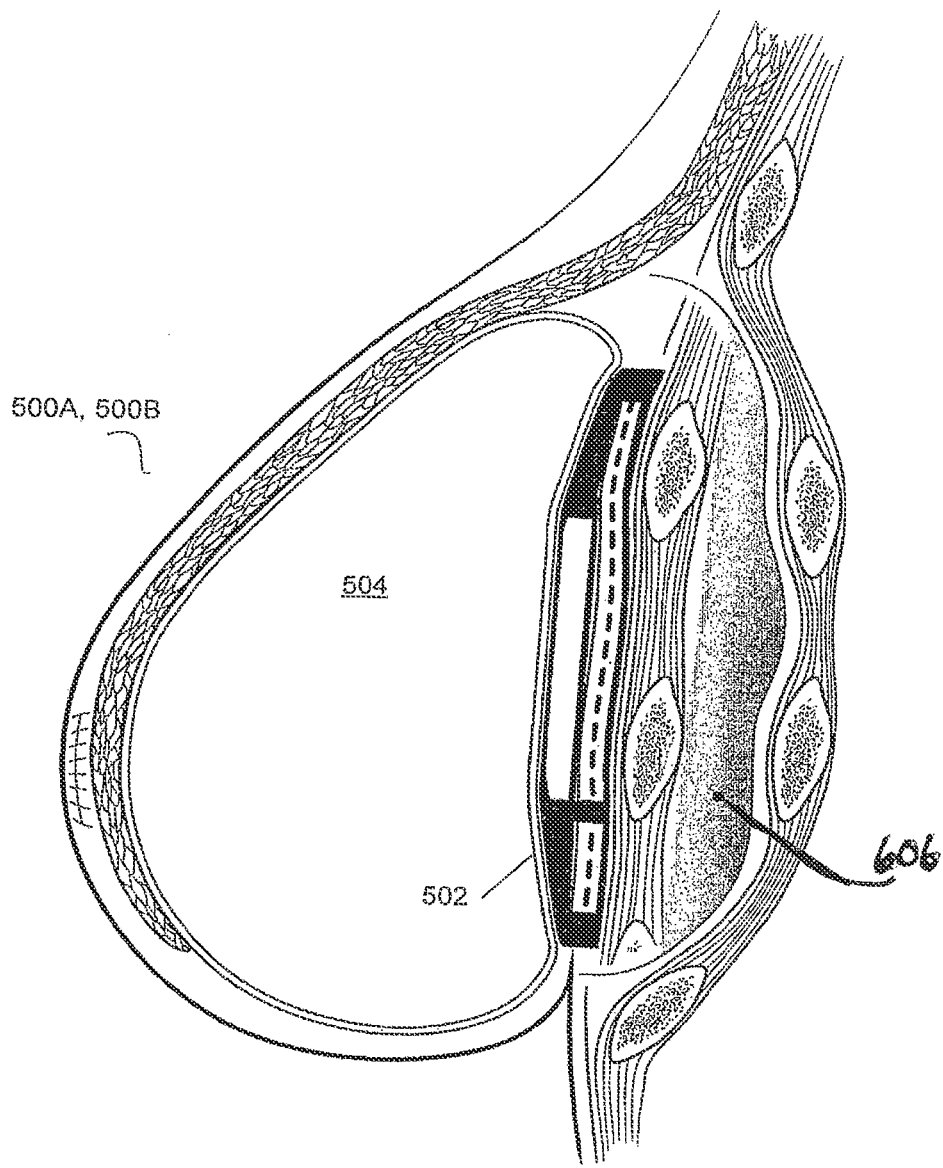
FIG. 6C is side profile view of an inflated prosthesis, in accordance with embodiments of this disclosure.

Additionally, as balloon 504 inflates, base structure 502 flattens to absorb the pressure due to the inflation process. The absorption of the pressure may help maintain a substantially flat chest wall, which may provide a more natural looking breast during reconstruction. The base structure 502 has built-in resistance to equalize posterior force of expansion on breast tissue to avoid deformation of the chest wall. For example, the negative resistance provided by base structure 502 against the pressure of the inflated balloon may avoid a concave deformity of the chest wall and ribs, as shown in FIG. 6C. A depression 606 into the chest wall may result during expansion when using currently-available tissue expanders. The avoidance of the concavity can decrease the need to supply additional soft-tissues to fill the concavity, leaving adequate tissue to reconstruct the breast as well as a contralateral breast if required. Alternatively, the avoidance of the concavity may leave a substantial amount of tissue to reconstruct the breast to be symmetric to a contralateral breast.

Types of Prosthesis

Each patient undergoing a mastectomy may present different physical characteristics, and as such, the prosthesis selected may need to be customized. For example, circumstances including, without limitation, the size of the breast, the shape of the breast, the size of the patient, and/or the advancement of the cancer cells in the breast, may need to be considered prior to a mastectomy. As such, according to one embodiment, a prosthesis used in the delayed-immediate, delayed-delayed, or preventive mastectomy methods may be customizable for each patient.

In one embodiment, the prosthesis may be side specific prosthesis (i.e., right-breast prosthesis and left-breast prosthesis). In other embodiments, the prosthesis may come in various sizes to accommodate different breast volume. Prior to the step of performing a mastectomy, a proper prosthesis may be determined, including, for example, determining a side-specific prosthesis and/or measuring the width of a chest wall for determining the appropriate size of the prosthesis.

In other embodiments, prosthesis 500A or 500B may include various anterior projection profiles (the projection of the breast from the chest wall), depending on the reconstructive needs and the desires of a patient. In one embodiment, the chest wall may be measured and a size and shape of a prosthesis may be selected based on the size. The size and shape may vary depending on the desired aesthetic outcome or matching of a contralateral breast.

In addition to the above, for patients who are at risk for post-mastectomy treatment or for patients who are required to undergo post-mastectomy treatment, a prosthesis, appropriate for the type of treatment, may be chosen. In one embodiment, for patients who are at a low-risk of requiring post-mastectomy treatment or for those whose treatment includes external beam irradiation, an external beam irradiation prosthesis may be used. Alternatively, for patients who may need an internal beam irradiation or an internal and external beam irradiation combination, a brachytherapy prosthesis may be used. Details of the external and internal beam irradiation prostheses are presented below.

External Beam Irradiation Prosthesis

Referring to FIG. 7, an anterior view of a vertical cross section of external beam irradiation prosthesis 700 is shown. Prosthesis 700 may be similar to prosthesis 500A shown in FIG. 5A. Prosthesis 700 includes base structure 702 and a balloon coupled to base structure 702 (for the sake of brevity, the balloon is not shown). The base structure 702 may comprise a framework that allows for separate angulations for each section to contour to the chest wall, as shown in FIG. 7. Prosthesis may also include a breast and breast and axillary drainage tube 706, including an axillary extension 707, coupled to axillary drainage port 708 (shown in FIG. 5A) for draining bodily fluids, instillation/evacuation tube 710 coupled to instillation/evacuation port 712 (shown in FIG. 5B) for inflating and deflating a balloon coupled to base structure 702. Prosthesis 700 may also include suture secure tabs 714 for attaching prosthesis 700 onto a chest wall, reducing or substantially eliminating post-mastectomy displacement of the prosthesis.

In one embodiment, breast and axillary drainage tube 706 may be integrated into the perimeter of prosthesis 700, as seen in FIG. 7, FIGS. 8A and 8B, and FIG. 9. FIG. 8A shows a side view of inflated prosthesis 700 that include breast and axillary drainage tube 706 at the perimeter. The flexible base structure 702 may move down based on pressure from inflation of the balloon 704. FIG. 8B illustrates a cross-section of breast and axillary drainage tube 706, which may include a fenestrated peripheral drain (e.g., fenestrated peripheral drainage system 709) with central open core for passage of devices, such as an unclogger, i.e., breast and axillary drainage tube 706 may include openings which may draw fluid build-up in the breast cavity (a close-up view of breast and axillary drainage tube 706 is shown in FIG. 9). The fenestrated peripheral drain may also comprise a double-perforated core with off-setting perforations. In one embodiment, breast and axillary drainage tube 706 may be seated into base structure 702 where the base structure may be made of a flexible, plastic material. It is noted that base structure 702 may be made of other suitable materials known in the art. The drainage tube 706 may drain through a collar at a support strut as shown. FIG. 8C shows another view of the installation/evacuation tube 710 connected to a port.

One distal end of breast and axillary drainage port 706 may extend to an axillary part of the body, i.e., below the underarm. Here, breast and axillary drainage tube 706 may be coupled with axillary drainage port 708, which may be placed underneath the skin (as shown in FIG. 7 and FIG. 9). In one embodiment, port 708 may be a metal port. Alternatively, port 708 may include a biocompatible material. Due to the placement of port 708 (e.g., on the lateral wall as shown in FIG. 5A), port 708 may be outside of the field of radiation, therefore, does not deflect radiation beams.

Breast and axillary drainage tube 706 and axillary drainage port 708, (collectively, the drainage system) may allow for readily accessible external drainage of fluid build up, including, without limitation, seroma fluids in the breast cavity. The drainage system avoids the need for an external drain in contact with the prosthesis, which may decrease the risk of infection. In addition, the evacuation of the accumulated fluids avoids the need for an expensive, risky surgical drainage to remove the fluids. The removal of the accumulated fluids will be discussed in further detail with respect to the needle-locking technique of the external beam prosthesis.

Similar to breast and axillary drainage tube 706, instillation/evacuation tube 710 may be integrated to base structure 702. Instillation/evacuation tube 710 may have one distal end coupled to balloon 704 for inflation or deflation purposes. In other embodiments, instillation/evacuation tube 710 may be independent of base structure 702. For example, one distal end of instillation/evacuation tube 710 may be provided through the center of base structure of 702 (as seen in FIG. 7) and may protrude from the top of base structure 702 into balloon 704, as shown in FIG. 8A. This may allow for the direct inflation of balloon 704 via instillation/evacuation tube 710. Similarly, balloon 704 may be deflated via instillation/evacuation tube 710. The other distal end of instillation/evacuation tube 710 may coupled to instillation/evacuation port 712. In one embodiment, port 712 may be a metal port. Alternatively, port 712 may be made of a biocompatible material. Due to the placement of port 712 (e.g., on the lateral chest wall as shown in FIG. 5A), port 712 may be outside of the field of radiation, therefore, does not affect radiation treatments that may be administered.

When a patient undergoes a mastectomy, and during the waiting period for pathology test results and/or the recovery time from the mastectomy, prosthesis 700 may be inserted into the breast cavity to preserve the breast skin envelope and other landmarks of the breast. In one embodiment, using instillation/evacuation tube 710 and instillation/evacuation port 712 (collectively, the instillation/evacuation system), a fluid may be injected through port 712 and may travel through tube 710 to balloon 704, inflating the prosthesis. Similarly, if a patient requires a post-mastectomy radiation treatment, the instillation/evacuation system may be used to draw the fluid from balloon 704, leaving a deflated prosthesis. For example, referring to FIG. 17, a rapid fluid instillation/evacuation device is shown. Using a needle-locking technique (discussed below), a needle, coupled to a manual valve, may be inserted into port 712. Port 712 may be configured in different geometries such as a drum port and the like, as would be recognized by one of ordinary skill in the art. The valve may be switch to a first position, allowing for a rapid instillation of a fluid, such as, but not limited to, saline, water, other liquids, air, soluble gases, liquid radiation material or other radioactive material through tube 710 into balloon 704. Similarly, if the prosthesis needs to be deflated, the valve may be switched to a second position, allowing for a rapid of the fluids from the balloon into a collection bag.

It is noted that prosthesis 700 may also be inflated, for example, by providing air or biocompatible material through the instillation/evacuation system into balloon 704. The injecting the fluids, air, and/or biocompatible material will be discussed in further detailed with respect to the needle-locking techniques of the external beam prosthesis.

Needle-Locking Techniques

In one embodiment, ports 708 and 712 may each be respectively accessed via a needle-locking method, as shown in FIGS. 10A and 10B. A needle, similar to needle 752A, 752B, or 752C (collectively needle 752) of FIG. 10B, which may be specific to port 708 or 712, may be used to remove and collect the fluid. For example, needle 752 may be specific to drainage port 708, and may be coupled to a suction bulb that provides a negative pressure that draws the liquid through the openings of breast and axillary drainage tube 706 through port 708 into a collection bag, as shown in FIG. 14B. Suction bulb 1402 may be worn around the abdomen via an abdomen strap and may lay substantially flat against the abdomen. In accordance with various embodiments, needle 752 is flush with the chest wall and can remain in-situ for drainage during perioperative period. The needle 752 may be re-inserted as required and may be coated with a soft rubber coating to avoid skin irritation. FIG. 14B further shows a specific locking configuration for a saline insertion/removal two way valve 1402 and a seroma fluid removal valve 1404. Still further, FIG. 14B shows a side view of ports 708 and 712 with suture fixation points 1406 and a skin view of ports 708 and 712 with plastic leaflets 760. A mechanism of needle attachments 1408 is further shown, where a practitioner may penetrate the port 708, 712, and then turn and/or pull the needle 752 to lock the needle 752 in place. In some embodiments, the needles 752 are flush with the chest wall.

Figure 15:
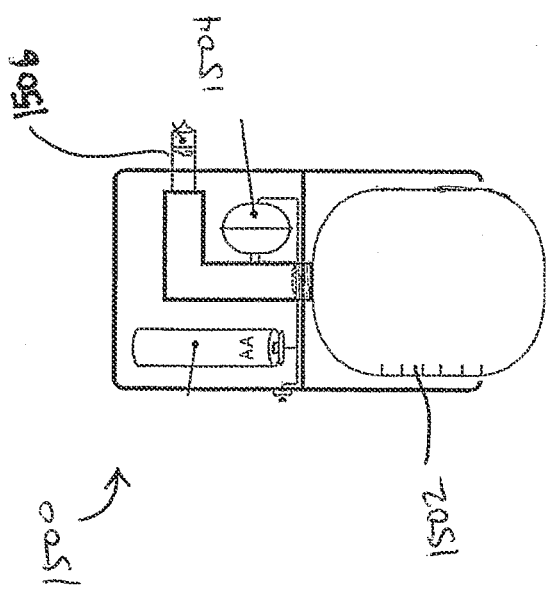
FIG. 15 shows a battery operated vacuum drainage system, in accordance with embodiments of this disclosure.

In other embodiments, needle 752 may be coupled to a battery operated fluid evacuator 1500 which may apply an appropriate negative pressure to draw out the fluids, as shown in FIG. 15. Particularly, the battery operated fluid evacuator may provide a vacuum pressure via a motor 1504 for pulling the fluids through drainage tube 706, through port 708, through a needle (similar to needle 752 of FIG. 10B), and into a drainage collection bag 1502. As shown in FIG. 15, the fluid evacuator 1500 comprises a male-female connection 1506 for a needle-locking system.

Alternatively, in other embodiments, needle 752 may be coupled to a gravitational drainage bag that may be worn on the legs of the patient, as shown in FIG. 14A. The gravitational drainage bag may draw the fluid from inside the breast cavity through drainage tube 706, port 708, and to a collection bag worn on a patient's leg. The above embodiments (shown in FIGS. 14A-14B and FIG. 15) allows for body fluids to be removed in a more efficient manner, reducing or eliminating infection normally caused from surgical implementations to remove the fluid. Additionally, the above methods allow a patient to remove the accumulated fluids more frequently, further reducing complications caused by fluid-build up. In some embodiments, after the postoperative period, the above methods may be used to drain the inadvertent collection of fluids in the breast or axillary regions.

In one embodiment, needle 752 may include an appropriate latch that may be used to connect to port 708 from above the skin. As shown in FIG. 10A, port 708 may include locking tabs 754, which allows only one latch configuration of a needle 752 to connect to the port 708 and avoids inadvertent removal of the needle 752 during draining, inflating, and/or deflating steps, and during activities of daily living. Additionally, the needle locking technique eliminates any erroneous access to the prosthesis such as, but not limited to, accidentally deflating the prosthesis when the body fluids needs to be drained, etc. In a non-limiting example, needle 752 may include latches, such as, but not limited to, a male-female connection of different geometries as seen in FIG. 10B. As such, port 708 may be customized to include locking tabs 754 of different geometry to accommodate the needle 752. The different needle locks may allow for distinguishing between the different ports located in the similar area. For example, instillation/evacuation port 712, which may be used to inflate and/or deflate the prosthesis, may be located in the general vicinity of drainage port 708. If the prosthesis may need to be deflated, a needle designed for port 712 may be used to access port 712 to draw the fluid from the balloon of the prosthesis. To ensure that port 712 is being accessed, as opposed to drainage port 708, the needle must lock into port 712 prior to the removal of any fluids. FIG. 10A shows the drainage port 708 positioned under the skin 1004, comprising plastic leaflets 760, and coupled to tubing 1002 that leads to the prosthesis. As shown in FIGS. 10A and 10B, the needle 752 may connect to a collection system via tubing 1006 to a bulb or leg bag (not shown).

In one embodiment, referring to FIG. 5A and FIG. 11B, port 708 and 712 may be housed as a single structure 1150, termed dual-port system, and may be positioned horizontally on the lateral chest wall and may have a plurality of tubes connecting to the prosthesis' tube, such as drainage tube 706 and instillation/evacuation tube 710. In one embodiment, tubes 706 and 710 may have a larger diameter than the plurality of tubes from the port. This may allow for unobstructed passages of devices from the ports into the prosthesis, like insertion of radiation rods or a cleaning device.

Figure 16:
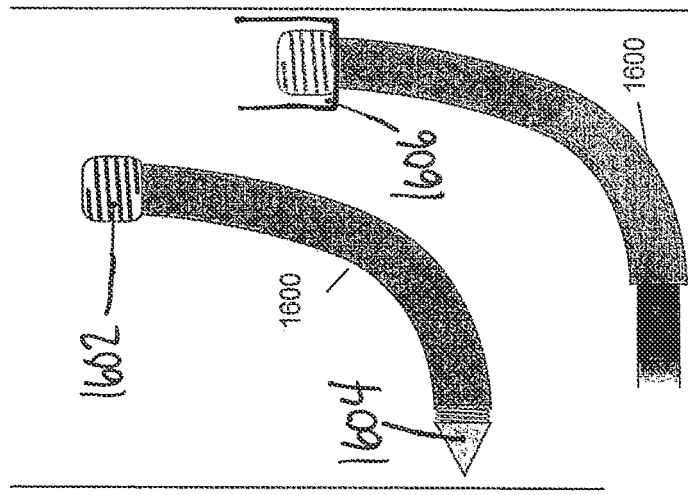
FIG. 16 shows a suction-tunneler device, in accordance with embodiments of this disclosure.

In one embodiment, having the ports housed as a single structure, allows for the tubes 706, 710 connected to the prosthesis to be easily maneuvered to the lateral chest wall through a suction tunneling technique, as shown in FIG. 16. In one embodiment, suction tunneler 1600 may be for passage of the tubing of the prosthesis to the ports located on the lateral chest wall, including, without limitation, drainage tube 706 and instillation/evacuation tube 710 via, for example, a screw tip 1604 used for penetrating through the subcutaneous tissues. A suction pump 1606 coupled to a suction attachment 1602 of suctioner 1600 may provide a negative vacuum pressure, drawing the tubes from the prosthesis to the chest lateral wall. An additional benefit of having the dual port system is the customization of the tubes connected to the port. Depending on the size of the chest wall, the tubes (e.g., drainage tube 706 and instillation/evacuation tube 710) may be trimmed to fit a patient. Furthermore, passage of the tubes through narrow tunnels can help eliminate healing problems in this region for patients who require radiation therapy.

In other embodiments, the ports 708 and 712 may be housed as a single structure situated horizontally on the inferior and lateral aspect of the chest wall. The locations of the ports, which may be made of metal or other biocompatible material, may be outside a radiation field, and thus, may not interfere with the post-mastectomy therapy. Alternatively, ports 708 and 712 and the prosthesis may be a single, integral unit.

Figure 12:
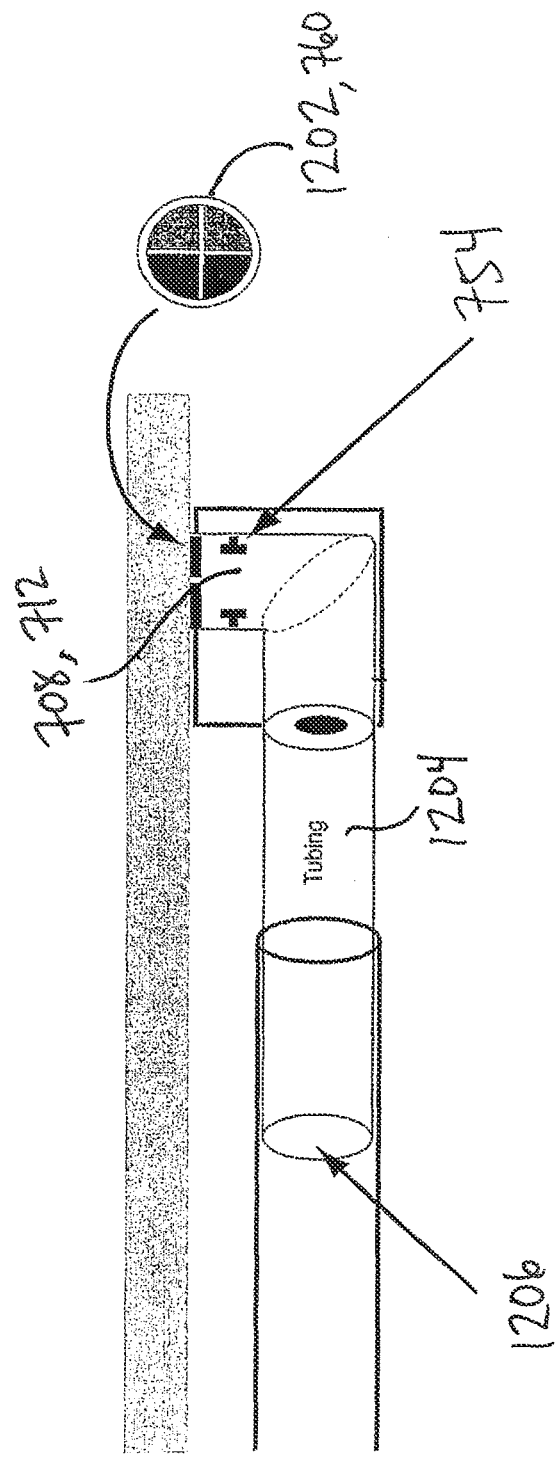
FIG. 12 shows a port and connection, in accordance with embodiments of this disclosure.

Generally, if there is an accumulation of fluids in a chamber of the ports, the overlaying skin can break down and expose the port. As such, in one embodiment, referring again to FIG. 10A, port 708 (and similarly, instillation/evacuation port 712), may be centrally depressed or concave from the skin level. This shape may allow the overlying skin to heal after the removal of the needle. Further, to reduce agitation to the skin, needle 752, may include a soft, sponge-like material to protect the skin from irritation. Additionally, ports 708 and 712 may also include four leaflets 1202, as shown in FIG. 12, which are similar to the leaflets 760 described above. The four mechanical (e.g., spring-loaded) leaflets may turn inward when a needle is inserted through the skin, reducing or substantially eliminating any fluid accumulation in the concavity of the port when the needle is removed. This allows the skin to heal adequately after removal of a needle. One of ordinary skill in the art would recognize that other geometries aside from the four leaflets may be suitable for reducing or eliminating any fluid accumulation in the port.

The needle-locking components and techniques described in the present disclosure are not limited to the application described. The needle-locking components and techniques may be used for other medical applications and/or with other medical devices known in the art.

Similarly, the components shown, for example, in FIGS. 9, 13A, 13B, 14A, 14B, 15, 16, and 17 are not limited to the techniques described in the present invention. One of ordinary skill in the art would recognize their use in the medical field in other applications as well as in combination with other medical devices and techniques.

Brachytherapy Irradiation Prosthesis

As noted above, survival advantages with post-mastectomy treatment occur when internal mammary nodes are treated within the radiation fields. The present disclosure provides for the treatment of these internal mammary nodes, as well as the chest wall and axillary lymph nodal basins, by providing a prosthesis adapted to receive a plurality of brachycatheter rods. In one embodiment, the brachycatheter rods may administer the radiation field to treat the breast cavity internally. In other embodiments, the brachycatheter rods may be used to treat the breast cavity internally while an external beam may be used to treat the breast skin and clavicular nodes. These treatments may be done while the prosthesis is still inflated. Alternatively, these treatments may be done with the prosthesis deflated.

In one embodiment, referring to FIG. 18, brachytherapy irradiation prosthesis 1800 is shown. Brachytherapy irradiation prosthesis 1800 may be similar to prosthesis 500A, 500B, and 700 of FIGS. 5A, 5B, and 7, respectively, and may also include, for example, a plurality of brachytherapy sleeves 1811 built into the base structure. The sleeves 1811, coupled to brachytherapyport 1810 (both shown in FIG. 5B), may provide tracks for receiving a radioactive source (e.g., radiation rods liquid radiation source, gaseous radiation source, wire placement with an radioisotope attached to the wire, etc.). The sleeves 1811 may also position brachycatheter rods proportioned on the chest wall below the elevated framework of the prosthesis 1800 and axillary region for providing optimal treatment to patient. The framework allows for separate angulations for each section to contour to the chest wall. The framework may be stabilized by using axillary suture tacking 1850 at sidebar connectors 1852.

In some respect, the brachytherapy port 1810 may be integrated into the prosthesis as an integral unit. The brachytherapy port 1810 may be integrated underneath, to the side, or spaced apart from the prosthesis.

In one embodiment, the brachycatheter rods may be customized to a certain length and diameter to fit a prosthesis appropriate for the patient, i.e., the rods may need to be customized based on the breast size of the patient, the chest wall size of the patient, the side of the breast needing treatment, etc. Additionally, the brachycatheter rods may have different radiation emission widths depending on the location of the rod in the prosthesis, e.g., the axillary region or the chest wall, and thus can extend treatment to different areas in the chest cavity.

Brachytherapy irradiation prosthesis 1800 may also include a drainage system (breast and axillary drainage tube 706 and drainage port 708) for removing bodily fluid collected in the breast cavity and axillary region. Additionally, prosthesis 1800 may include an instillation/evacuation system (instillation/evacuation tube 710 and instillation/evacuation port 712) for inflating and deflating a balloon (not shown) coupled to base structure 1802. In order to secure prosthesis 1800 onto the chest wall of a patient, a plurality of suture tabs 714 coupled to base structure 1802 may be provided. The suture tabs 714 may be oriented in various positions about the prosthesis. The prosthesis 1800 additionally may include intracatheter connectors 1854.

Referring again to FIG. 11A, the brachycatheter port may be housed as a single structure with drainage port 708 and instillation/evacuation port 712 (collectively called the three-port system). In one embodiment, a brachycatheter radiation rod may be inserted into a prosthesis via a brachytherapy port and a needle-locking mechanism. For example, depending on the location of the tracks and the brachycatheter rods needed at that location, the size and length of the brachycatheter rods may vary. As such, the brachycatheter port may be a multi-channel port to accommodate the various brachycatheter rods. In one embodiment, a brachycatheter rod may be threaded through the brachycatheter port by a needle-locking technique, where one type of brachycatheter rods may fit into one channel of the multi-channel brachycatheter port. For example, referring to FIG. 12, a port coupled to a connection tube 1204 is shown. The port may be a brachycatheter port. Alternatively, the port shown may be a drainage port (similar to port 708) or an instillation/evacuation port (similar to port 712). The port of FIG. 12 may include a locking system that allows only one input to connect to that port. As such, if the port of FIG. 12 is a brachycatheter port, the locking system may allow only brachycatheter rods to be inserted, thereby eliminating surgical routines to insert the brachycatheter rods which can cause a risk of infection, scarring, and considerable expenses to the patient. The connection tube 1204 may connect to tunneled tubing 1206 from the prosthesis to enable passage of radiation rods and/or a drain unclogger.

Alternatively, in order to determine the location for the different brachycatheter rods, particularly brachycatheter rods of different lengths and/or different radiation emission widths, each sleeve 1811 may be color coded and the similar color may be reflected in port 1810. Referring to FIG. 11A, using a needle-locking technique similar to the technique described above, a needle may be inserted and locked into port 1810, exposing the color scheme of the port. Depending on the type of rod, a doctor may thread the rod through the track into the prosthesis.

Embodiments Common to the External Beam Irradiation Prosthesis and the Brachytherapy Irradiation Prosthesis In one embodiment, the needle locking technique described above may also include unclogger 1000 coupled to port 708 and/or port 712 to prevent or remove debris from remaining in the prosthesis and obstructing flow, as seen in FIGS. 13A and 13B. Unclogger 1000 may include a syringe 1002 having a plunger end 1001 and an inflatable balloon tip 1004. Referring to FIG. 13A, balloon tip 1004 may be deflated prior to inserting into a port, such as, but not limited to a drainage port or an instillation/evacuation port. Referring to FIG. 13B, using a latch appropriate for the security tabs of each port, the balloon 1004 may be inserted via a port into a tube. FIG. 13B shows a needle inserted into a drainage system port. Syringe 1002 may include some fluid and may be used to inflate balloon tip 1004 by depressing the plunger 1001. Balloon tip 1004 may be routed through the tubes and may clear any debris present in the tubes of the prosthesis. For example, balloon tip 1004 may be used to clear matter within the core of the drainage tube 706 of FIG. 7. Similarly, balloon tip 1004 may be used clear debris (e.g., matter build-up) from instillation/evacuation tube 710 of FIG. 7.

Radiation Brassiere

In one respect, a radiation brassiere, as shown in FIGS. 19-23, may be used in combination with the above prosthesis or separately to deliver radiation to the, for example, the skin of the breast, chest wall, and axilla, as well as regions of the chest wall, and regional nodal basins (e.g., axillary, internal mammary, infraclavicular, and supraclavicular nodes). In some embodiments, the radiation brassiere may be specifically designed to be used after patients having a total mastectomy or for patients undergoing partial mastectomies. The radiation brassiere may also be used alone or in combination with other treatment (e.g., external beam irradiation, chemotherapy, etc.) as determined by a radiation oncologist. In one embodiment, the radiation may be delivered in a hospital based setting where patients may be able to receive their radiation treatment as an outpatient. Alternatively, the radiation may be delivered in any other environment as suited for the patient.

Figure 19A:
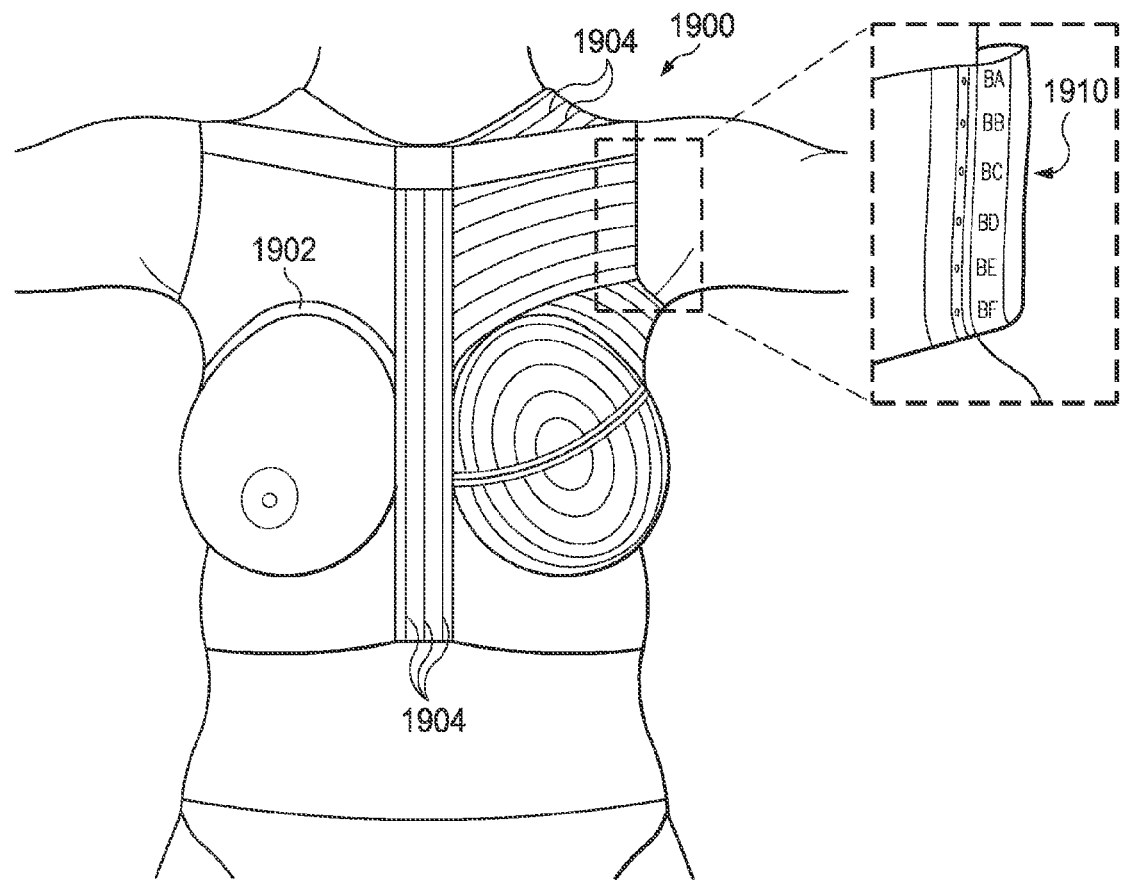
FIG. 19A is a front view of a single unit brassiere, in accordance with embodiments of this disclosure.

In one embodiment, radiation brassiere 1900, which may be similar to a body suit, may extend from the neck to the umbilicus, as shown in FIG. 19A. The brassiere 1900 may be made of an elastic band material which conforms to the body and prevents migration and movements during treatment. One of ordinary skill in the art would recognize that other suitable materials may be used instead of or in addition to the elastic band material. The radiation treatment brassiere may be side specific (right or left breast) or may be bilateral model for patients in need of radiation treatment deliver to both breasts.

The brassiere may have a separator ring 1902 surrounding a non-affected breast to push the breast away (laterally) from the external region, typically used for patients needing treatment on one breast. In some respect, brassiere 1900 may be a single unit design, but may have several paneled treatment zones to customize treatment to specific regions of the breast, chest wall, and nodal basins based on the patients pathology and need for individualized treatment.

In some respects, the radiation brassiere may include brachytherapy radiation sheaths that may be color-coded by zones and may built into the radiation treatment panels with openings strategically placed for easy access to allow for insertion of radiation rods. For example, Velcro flap covers 1910 may be present at radiation rod insertion sites 1904 to cover the slots of the inserted rods to avoid inadvertent removal during activities of daily living. Each rod insertion site 1904 may be labeled to match each specific rod length. One of ordinary skill in the art would recognize that other materials may be used to cover and secure the slots of the inserted rods including, without limitation, pins, snaps, fasteners, zippers, and the like. In some respect, each rod insertion slot 1904 may be labeled to match each specific length radiation rod. Further, the radiation panels in the regions for treatment may be thicker than the remainder of the brassiere, which may be a sheer elastic material available in various colors (i.e., black, nude, or white).

Figure 19B:
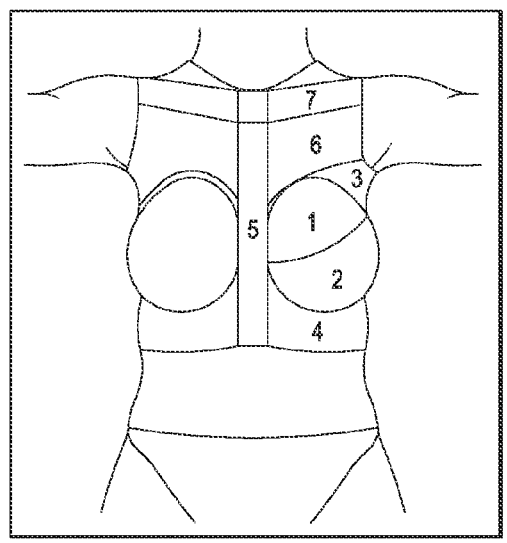
FIG. 19B is a front view of a treatment zones of the brassiere of FIG. 19A, in accordance with embodiments of this disclosure.

In one embodiment, the radiation brassiere may include multiple areas of treatment, as shown in FIG. 19B. For example, the areas of treatment may include, without limitation, a superior breast skin area, including underlying pectoralis major muscle (Zone 1), an inferior breast skin area (Zone 2), an axilla skin area, including underlying axillary lymph nodes (Zone 3), an inferior chest wall skin (Zone 4), an external skin area, including the internal mammary lymph nodes (Zone 5), a superior chest wall skin area, including infraclavicular lymph nodes (Zone 6), and the supraclavicular lymph nodes area (Zone 7). Each radiation treatment zone may be customized for each patient's need based on, for example, the treatment regimen and the depth of penetration of the radiation emission. The zones depicted here are exemplary and one of ordinary skill in the art would recognize that other divisions may be suitable, i.e., a plurality of zones may be combined, not used, or there may be one zone for the entire chest area.

Figure 20A:
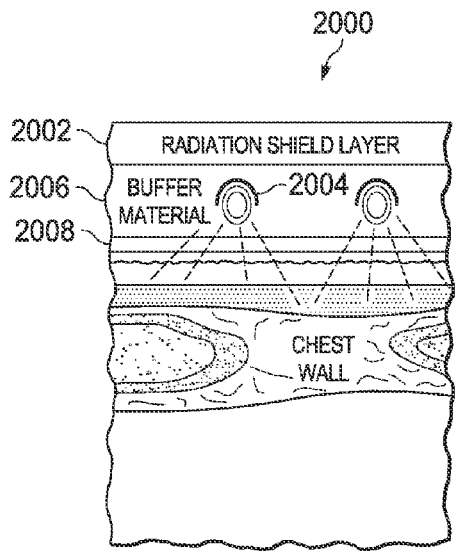
FIGS. 20A through 20D show cross-sections of a radiation brassiere, in accordance with embodiments of this disclosure.
Figure 20C:
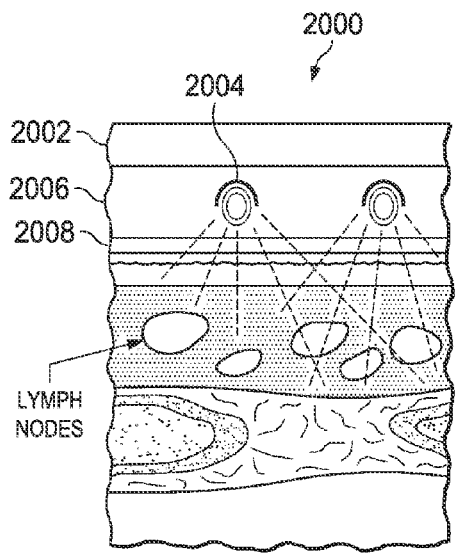
Figure 20B:
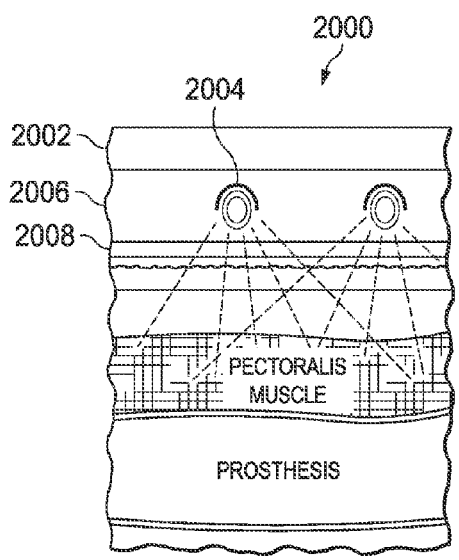
Figure 20D:
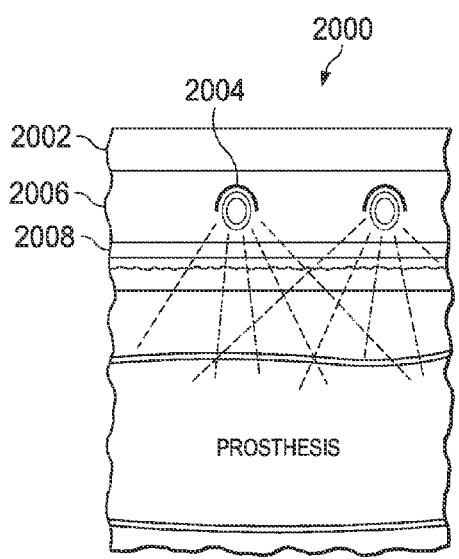
Figure 21:
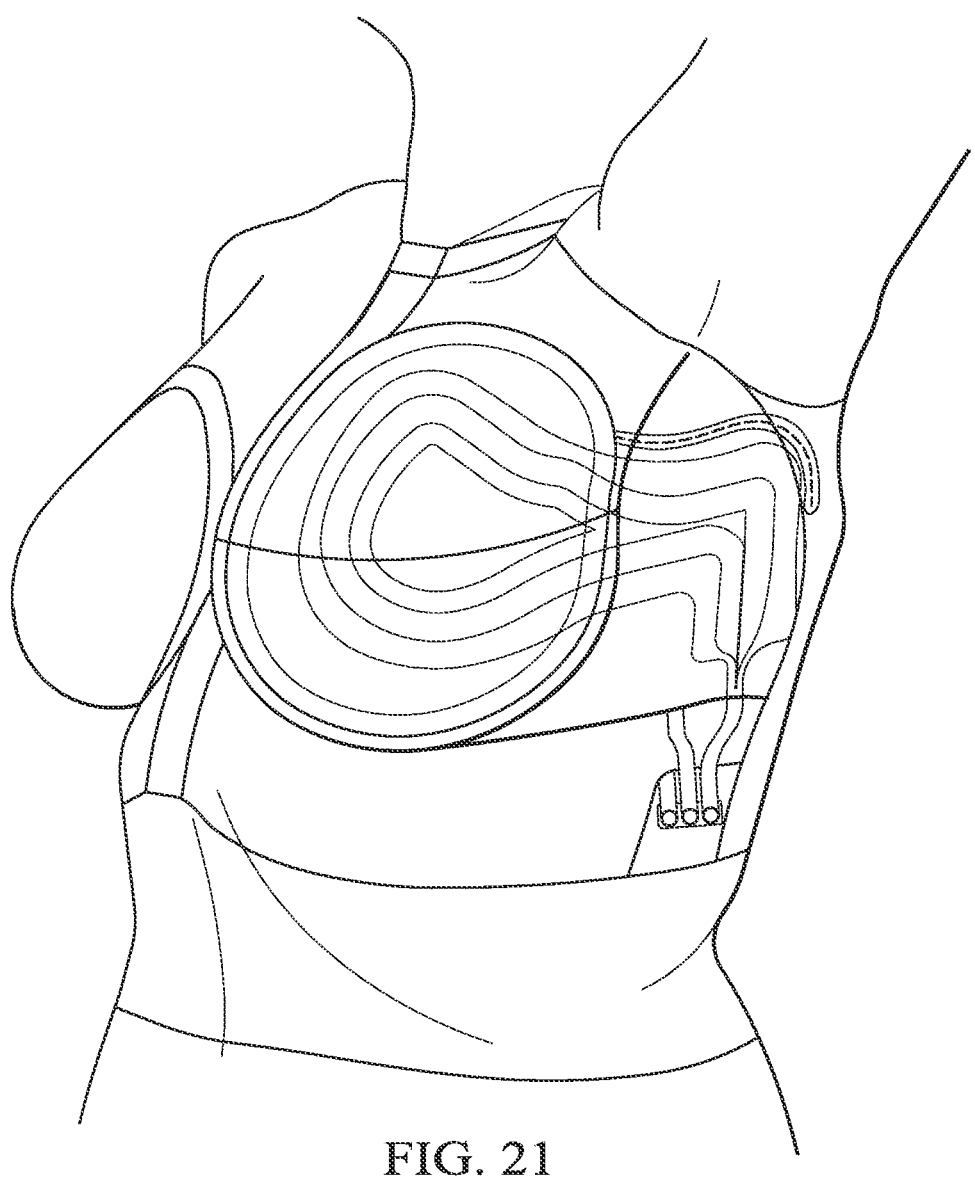
FIG. 21 shows a brassiere and a brachytherapy prosthesis, in accordance with embodiments of this disclosure.

Referring to FIGS. 20A through 20D, cross-sectional diagrams of radiation brassiere 2000 are shown. In one respect, radiation brassiere 2000 shown in FIG. 20A may be used for the treatment of the breast skin, subcutaneous tissues, and the chest wall areas (Zone 4). Similarly, radiation brassiere 2000 of FIG. 20C may be used to treat the breast skin, subcutaneous tissues, and the chest wall areas as well as nodal basin areas (e.g., Zones 3, 5, 6, and 7). In FIG. 20B, radiation brassiere 2000 may be used to treat the breast skin, subcutaneous tissues, and the pectorialis muscle (Zone 1). The radiation brassiere shown in FIG. 20D may be used for the treatment of breast skin and subcutaneous tissues areas (Zone 2).

Each of the radiation brassieres shown in FIGS. 20A through 20D may include radiation treatment panels 2000 that include outer radiation shield 2002 to prevent exposure to other anatomic regions of the patient (i.e., extremities) and others who come in contact with the patient. In one respect, the radiation shield layer 2002 may also shield the radiation that is delivered via a brachytherapy prosthesis model disclosed above. See FIG. 21.

The radiation treatment panels may also include radiation rod sleeves (e.g.. sleeves 1811 in FIGS. 5B and 18) that may be surrounded by radiation beam direction reflector plate 2004 to angle the beams only towards the patient. The radiation rod sleeves may be positioned within buffer layer 2006 that may allow for a substantially even distribute the radiation beams to the treatment regions.

The radiation treatment panels may also include an adhesive layer used to adhere the radiation treatment panels to the skin. In one respect, the adhesive layer may allow for an even distribution of radiation at predetermined penetration depths to the areas needed treatment. The adhesive layer may also stabilize the radiation treatment panels to a patient to prevent shifting or movement during a treatment as well as prevent erroneous delivering of radiation to unaffected areas.

The layers depicted in FIGS. 20A through 20D are example layers. One of ordinary skill in the art would recognize that layers 2002, 2004, 2006, and 2008 may be configured in any order and may include other interposable layers.

Figure 22:
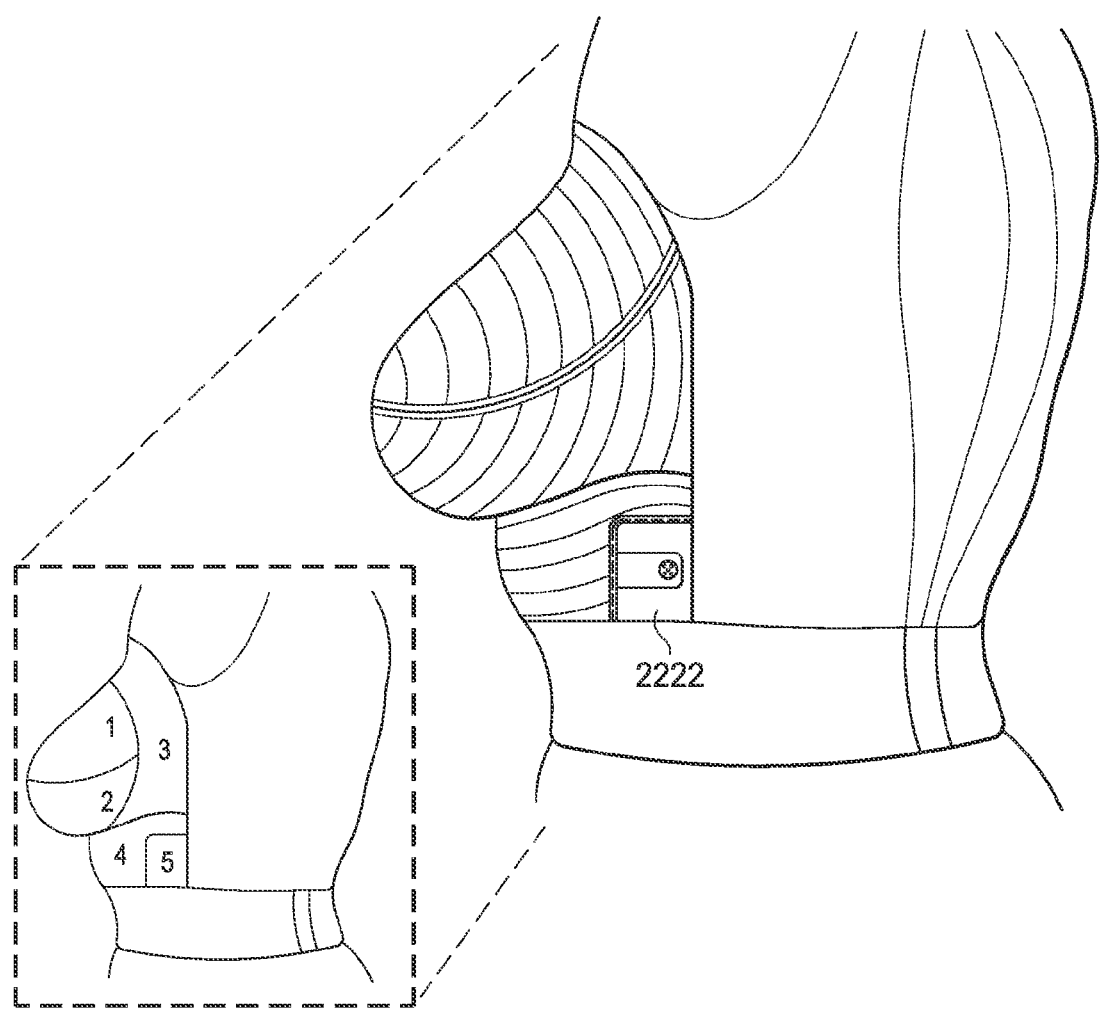
FIG. 22 shows a lateral view of a radiation brassiere, in accordance with embodiments of this disclosure.

The brassiere sizing (dimensions) may coincide with an underlying implanted prosthesis similar to the prosthesis shown in, for example, FIGS. 5, 7, and 18. As mentioned previously, the radiation rods can have various emission widths and may be customized based on the treatment plan. In one respect, an opening in the brassiere may be provided allowing for access to subcutaneous port 2222 of the implanted prosthesis (e.g., 2- or 3-port system) placed on the lateral chest wall at the time of mastectomy, as shown in FIG. 22. The implanted prosthesis placement may allow for simultaneously treatment of the chest wall underlying the balloon-like prosthesis and axillary and internal mammary nodal basins (brachytherapy rods sheaths built into the base structure of the prosthesis) and to treat the skin of the breast and chest wall, chest wall, and internal mammary, clavicular, and/or axillary nodal basins using the radiation brassiere.

Figure 23:
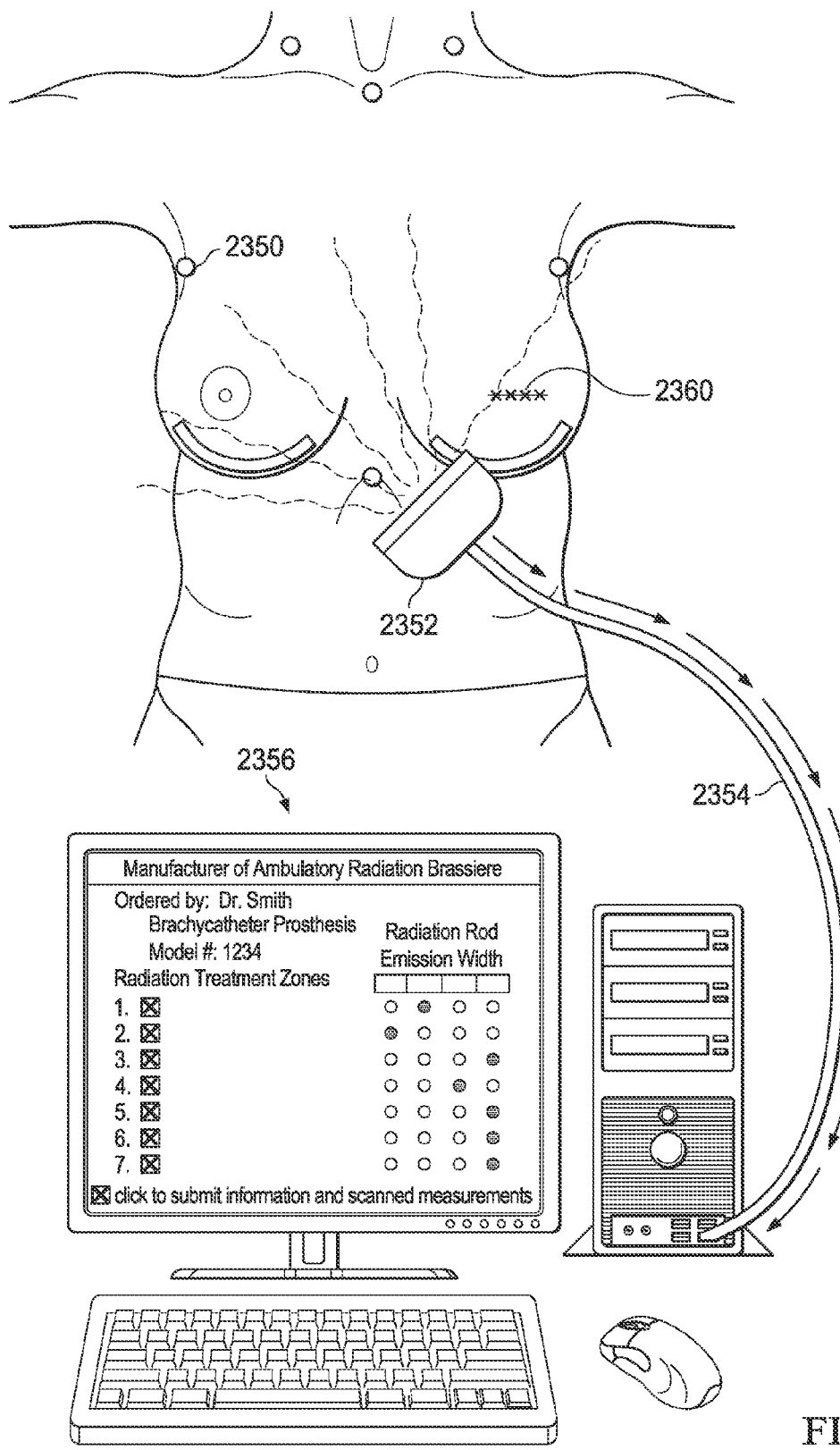
FIG. 23 show a technique for fitting a patient for a prosthesis and/or brassiere, in accordance with embodiments of this disclosure.

The use of a prosthesis and a radiation brassiere such as those disclosed in this disclosure may allow patients to better maintain their activities of daily living and work schedules. In one respect, approximately one week after surgery when the surgical pathology is complete, a patient may be fitted for a radiation brassiere (e.g., measurements of the chest wall, determining if a single or bilateral brassiere, radiation rod length, and the like). In one embodiment, a patient may be measured using infrared scanner 2352 with stick on indicators 2350 at various anatomic points, as shown in FIG. 23. The scanner may take measurements that may be directly download via port connection 2353 (e.g., a wired connection such as a USB connection or a wireless connection) to computer 2356. The information may be uploaded to the Internet, and more particularly to the brassiere manufacturer.

Alternatively, the measurements of a patient may be done manually by a doctor and may be provided to the manufacturing device using for example, the phone, internet, order forms and the like. Additionally, the measurements may take place prior to surgery, during surgery, or post surgery. For example, the scanning may be performed postoperatively after a mastectomy and placement of a brachytherapy prosthesis 2360.

In some respect, the radiation rods, and in particular, the radiation emission widths from the brachytherapy rods and also for the brachytherapy rods for insertion via the subcutaneous port into the implanted prosthesis 2360 may also be provided to the manufacturer at the same time the measurements for the customizable radiation brassiere or at an early or later time. The brassiere and rods for insertion into the brassiere and/or the implanted prosthesis may subsequently be sent to a medical institution providing the radiation treatment. In one respect, the radiation rods may be sent "hot" (activated with, for example, Iridium or other radioactive material known in the art) or "cold" (non-activated) with activation at the treating medical institution. In one embodiment, the rods may be inserted into the brassiere by the manufacturer and then sent to the treating medical institution or radiation oncologist. Alternatively, the rods may be sent separate from the brassiere for assembly and/or activation at the treatment facility.

Breast Reconstruction Kit

In one embodiment, breast reconstruction system may be package as a kit. The kit may include, without limitation: a breast prosthesis with a built-in drainage system, a suction tunneler for passing the plurality of tubes from the prosthesis to the lateral chest wall to connect with a port, a device for applying negative pressure to draw fluids from the breast cavity through the built-in drainage system. For example, the kit may include battery operated seroma fluid evacuator with disposable fluid collection bags, a flat negative-suction bulb attachment for abdominal wear, or a gravity leg bag used to externally drain fluids from the breast cavity through the built-in drainage system.

The kit may also include a syringe-loaded with balloon tip unclogger to remove any debris within the drainage system or any other tubes coupled to the breast prosthesis. The kit may also include ordering information to obtain brachycatheter radiation rods to insert into sleeves of the prosthesis. Alternatively, the kit may include at least one brachycatheter radiation rods (shielded for transportation and storage).

Figure 17:
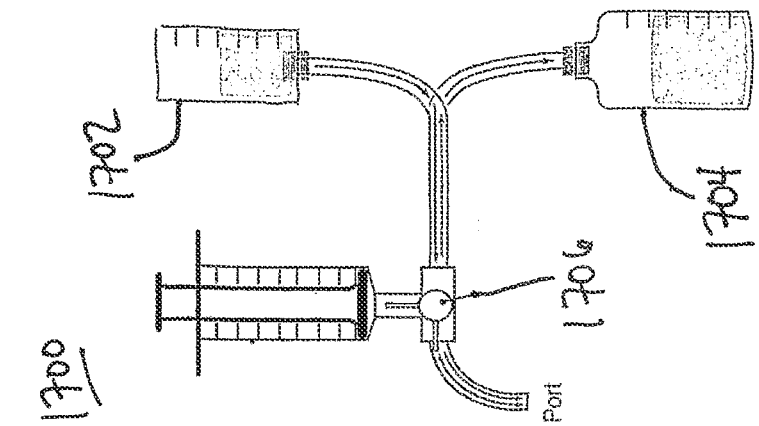
FIG. 17 shows a rapid fluid filler/evacuator used to inflate/deflate the prosthesis, in accordance with embodiments of this disclosure.

The kit may also include a rapid filler 1700, similar to FIG. 17 for inflating/deflating the prosthesis using a fluid. The rapid filler 1700 may include a sterile saline instillation bag 1702 and a sterile vacuum-sealed saline evacuation bottle 1704. Additionally, a valve 1706 is used for rapid saline filling of the prosthesis from the sterile saline instillation bag 1702. The valve 1706 also allows for rapid removal of saline from the prosthesis into the vacuum-sealed bottle 1704 for sterile disposal. Alternatively, other devices may be included and may be used to fill the prosthesis with other materials, including, without limitation, biocompatible materials, radioactive materials, air, soluble gases, and the like. Additionally, a plurality of locking needles may be provided in the kit. For example, a needle for accessing each of the individual ports may be included.

Additionally, the kit may include schematic diagrams of the prosthesis and detailed approaches, similar to FIGS. 1-4 outlining how to use the breast prosthesis to preserve the 3-D breast skin envelope and natural landmarks of the breast. The detailed approach may include methods steps for patients with stage-I or stage-II breast cancer. The detailed approach may include instructional steps for patients with stage-III or stage-IV breast cancer. Alternatively, the detailed approach may include instructions for patients who undergo preventive mastectomies.

The following examples are included to demonstrate specific embodiments of this disclosure. It should be appreciated by those of ordinary skill in the art that the techniques disclosed in the examples that follow represent techniques discovered by the inventors to function well in the practice of the invention, and thus can be considered to constitute specific modes for its practice. However, those of ordinary skill in the art should, in light of the present disclosure, appreciate that many changes can be made in the specific embodiments which are disclosed and still obtain a like or similar result without departing from the spirit and scope of the invention.

Figure 24:
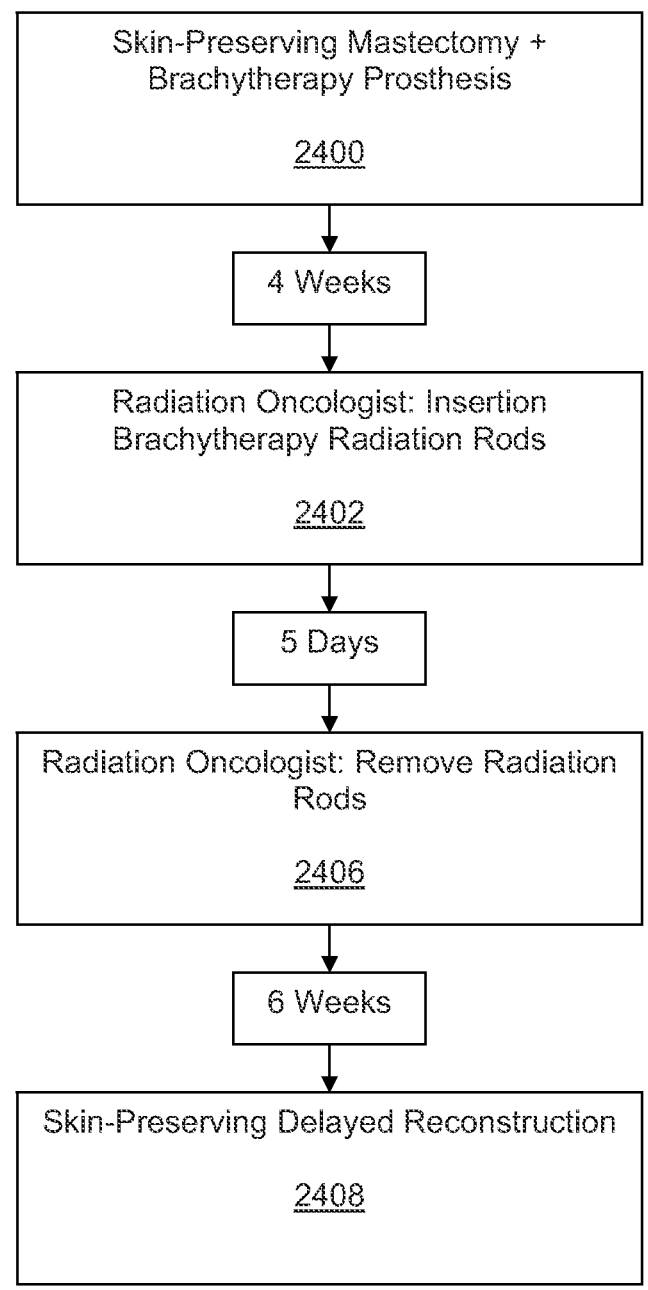
FIG. 24 shows a method flow chart for radiation delivery, in accordance with embodiments of this disclosure.

A possible clinical scenario in treating patients who need postmastectomy radiation therapy may include placement of a brachytherapy model prosthesis at the time of mastectomy (shown in FIG. 23). This may allow radiation delivery to be shortened considerably from the current six weeks of hospital based treatments with external beam irradiation for patients with breast cancer. For example, referring to FIG. 24, a patient may undergo a skin-preserving mastectomy. A brachytherapy prosthesis may be inserted into the breast at the time of the mastectomy (step 2400). A four week time period may lapse where the patient may recover from the mastectomy. At this time, the prosthesis may be inflated to preserve the breast skin and other natural landmarks of the breast. Upon healing from or as indicated by a treatment plan, the patient may undergo radiation treatment, where radiation rods may be inserted into the prosthesis, which may or may not be deflated (step 2402). The radiation treatment may last about five days and the removal of the radiation rods may subsequently be removed (step 2406). The patient may subsequently be scheduled for a definitive breast reconstruction after a time period, usually about 6 weeks (step 2408). During the time between the treatment and the reconstruction surgery, the prosthesis may be reinflated either gradual or filled all at once to a volume substantially equal to or similar to the inflation volume prior to the radiation treatment.

Figure 25:
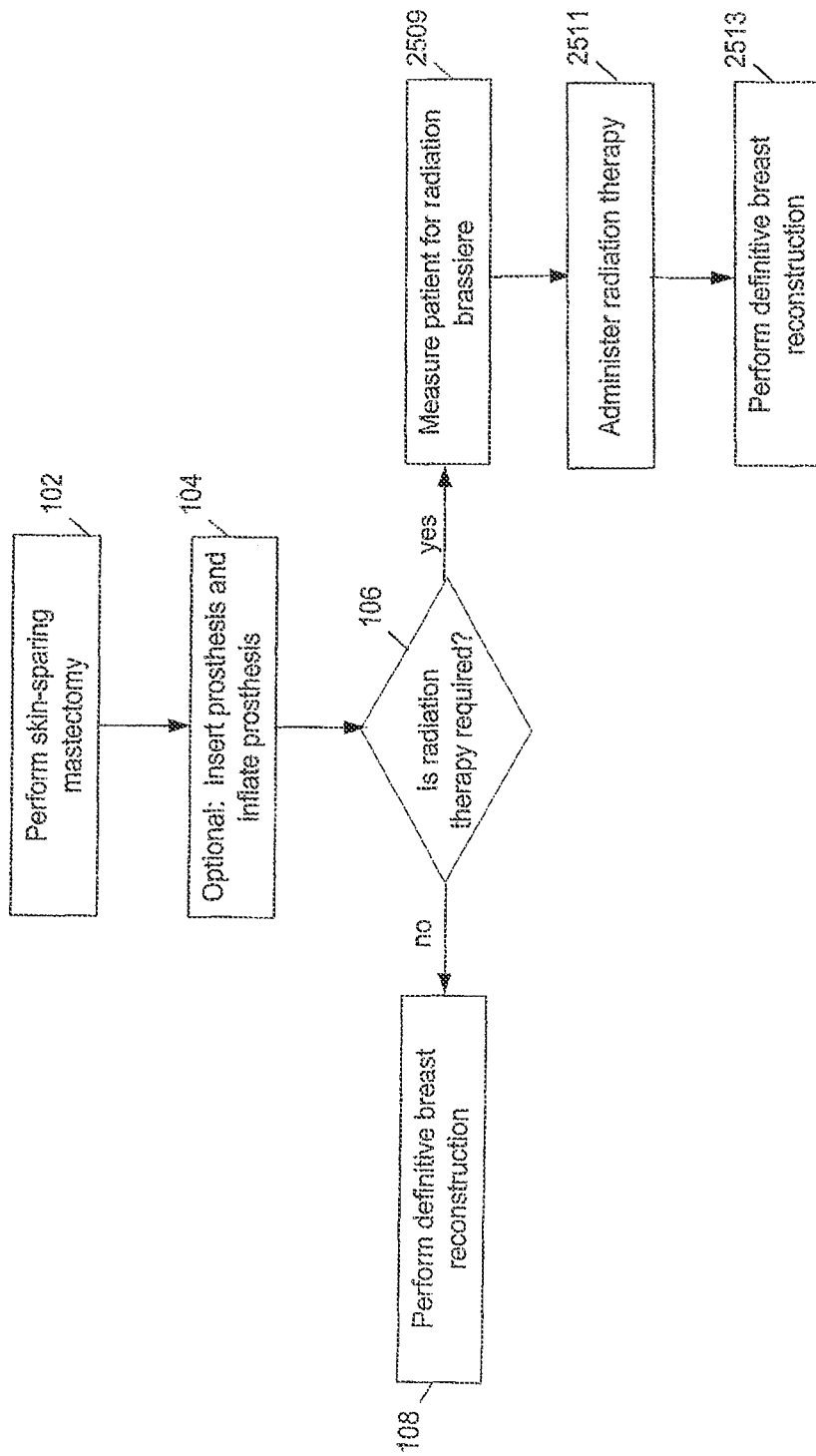
FIG. 25 shows a method flow chart for post mastectomy radiation treatment, in accordance with embodiments of this disclosure.

In another clinical scenario where a patient requires a may or may not require post mastectomy radiation treatment, and in particular an external beam irradiation, the present disclosure provides the following technique, as shown in FIG. 25. Steps 102, 106, and 108 are similar to those described in FIGS. 1 and 2. If a patient does require radiation treatment, in step 2509, a patient measured for a radiation brassiere either manually or via the infrared scanning technique of the present disclosure. In particular, step 2509 allows for customization of the brassiere as well as provides for designing of the radiation field appropriate for the patient (i.e., based on the pathology report).

Upon receiving the brassiere and activating the radiation rods configured for the treatment, the patient may undergo radiation treatment that lasts about 5 days (step 2511). One of ordinary skill in the art can recognize that the time period disclosed here are examples. It is known that radiation treatment may vary for each patient and therefore, the method may be adjusted accordingly.

After the radiation treatment, the radiation bra is removed and the patient may subsequently be scheduled for a definitive breast reconstruction after a time period, usually about 6 weeks (step 2513). The total process last about 3 months as compared to the 2 years of current methods.

In some embodiments, the method shown in FIG. 25 may also include a prosthesis, such as a brachytherapy prosthesis. In optional step 104, the prosthesis may be inserted into the patient and inflated to a volume sufficient for preserving the breast skin envelope and other natural landmarks of the breast. Upon determining if a patient requires radiation treatment, and especially if a patient requires internal irradiation, in step 2509, the appropriate radiation field and length for the prosthesis may also be measured and sent to a manufacture.

Prior to the administration of the radiation therapy, the prosthesis may be deflated and the rods may be inserted via ports coupled to the prosthesis. After treatment (step 2511) and during the time between the treatment and the reconstruction surgery, the prosthesis may be reinflated either gradual or filled all at once to a volume substantially equal to or similar to the inflation volume prior to the radiation treatment.

Other Applications for the Prosthesis

The above prosthetics have been discussed with respect to patients with breast cancer who undergo mastectomy surgeries and have opted for reconstruction surgery. However, the prosthetics may be adaptable to other patient who desire breast reconstruction surgery. For example, patients with partial or total breast defects (e.g., breast conservation therapy or lumpectomy with either partial or total breast radiation therapy) who may undergo treatment (e.g., intraluminal into lumpectomy defect) may benefit from the prosthetics of the present disclosure which may shape and reconstruct tissue and skin in more natural manner.

Similarly, patients with no surgical defects may benefit from the techniques and devices of the present disclosure. For example, carcinoma in-situ patients (e.g., LCIS or DCIS), who generally do not require surgery, may need radiation treatment of the skin and some lymph nodes and in some embodiments, may need other treatment techniques such as chemotherapy. Using the radiation brassiere of the present disclosure, the patient may receive the external radiation treatment, which does not interfere with other treatment regimens the patient may undergo.

With the benefit of the present disclosure, those having ordinary skill in the art will comprehend that techniques claimed here and described above may be modified and applied to a number of additional, different applications, achieving the same or a similar result. For example, any information presented to a user can be presented in text and/or graphic format. For example, one or more graphs, charts, clip-art, videos, animations, hierarchy trees, etc. may be used in addition to, or instead of the text and numerical data shown in the figures and described here. The claims attached here cover all modifications that fall within the scope and spirit of this disclosure.

What is claimed is:

1. A prosthesis comprising:
   a balloon configured to preserve a skin envelope;
   an instillation/evacuation port coupled to the balloon for inflating and deflating the balloon; and
   a sleeve coupled to a treatment port to accept at least one of a radioactive source or a chemotherapeutic source for treatment of an internal cavity, wherein the sleeve is fluidically isolated from the balloon.

2. The prosthesis of claim 1 further comprising a base coupled to the balloon.

3. The prosthesis of claim 2 wherein the base is configured to collapse when the balloon is inflated.

4. The prosthesis of claim 1 further comprising secure tabs for attaching the balloon onto a chest wall.

5. The prosthesis of claim 1 wherein the treatment port is further configured to accept at least one of a biologic source, an immunologic source, or a targeted treatment for treatment of an internal cavity.

6. The prosthesis of claim 1 further comprising a port structure further that houses the treatment port and the installation/evacuation port.

7. The prosthesis of claim 6 wherein at least one of the instillation/evacuation and treatment ports of the port structure comprises a locking system.

8. The prosthesis of claim 6 further comprising a port and tubing coupled to the instillation/evacuation port to inflate or deflate the prosthesis using a fluid.

9. A device for administering an external brachytherapy treatment comprising:
a radioactive source configured to treat all or a specific region of a breast, chest wall, or nodal basin; and
a separator ring configured to move an affected breast away from the radioactive source.

10. The device of claim 9 wherein the separator ring is coupled to a plurality of treatment panels configured to receive the radioactive source.

11. A method comprising:
inserting a preserver into a breast;
inflating a balloon of the preserver to a volume for preserving the breast skin envelope; and
performing a treatment of an internal cavity by providing a radioactive source or a chemotherapeutic source to a sleeve by way of a treatment port of the preserver, wherein the sleeve is fluidically isolated from the balloon.

12. The method of claim 11 wherein the preserver comprises an instillation/evacuation port coupled to the balloon for inflating and deflating the balloon.

13. The method of claim 11 further comprising performing a mastectomy on a breast and preserving a breast skin envelope prior to inserting the preserver into the breast.

14. The method of claim 11 further comprising affixing the preserver to a chest wall with one or more suture secure tabs.

15. The method of claim 11 further comprising deflating the preserver prior to performing the therapy treatment.

16. The method of claim 11 further comprising performing an external beam radiation treatment.

17. The method of claim 11 wherein providing a radioactive source comprises inserting at least one radiation rod via the radiation port coupled to the preserver.

18. The method of claim 11 further comprising performing a brachytherapy therapy by providing an externally applied applicator to treat an affected region.

19. The method of claim 11 further comprising performing a treatment of the internal cavity by providing a biologic source, an immunologic source, or a targeted treatment to the treatment port.

* * * * *